United States Patent
Janusz et al.

(10) Patent No.: US 12,059,441 B2
(45) Date of Patent: Aug. 13, 2024

(54) PROBIOTIC BACTERIAL STRAINS THAT PRODUCE SHORT CHAIN FATTY ACIDS AND COMPOSITIONS COMPRISING SAME

(71) Applicant: International N&H Denmark ApS, Cincinnati (DK)

(72) Inventors: Michael John Janusz, Oregonia, OH (US); Anna Malgorzata Plechaty, Springboro, OH (US)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 340 days.

(21) Appl. No.: 16/860,377

(22) Filed: Apr. 28, 2020

(65) Prior Publication Data

US 2020/0345791 A1    Nov. 5, 2020

Related U.S. Application Data

(60) Provisional application No. 62/841,385, filed on May 1, 2019.

(51) Int. Cl.
| | |
|---|---|
| *A61K 35/741* | (2015.01) |
| *C12N 1/20* | (2006.01) |
| *C12P 7/6409* | (2022.01) |

(52) U.S. Cl.
CPC .............. *A61K 35/741* (2013.01); *C12N 1/20* (2013.01); *C12P 7/6409* (2013.01)

(58) Field of Classification Search
CPC .......... A61K 35/741; C12N 1/20; C12N 1/04; C12P 7/6409; C12P 7/52; C12P 7/54; A23L 33/135; A61P 1/00
See application file for complete search history.

(56) References Cited

U.S. PATENT DOCUMENTS

| | | | |
|---|---|---|---|
| 9,314,489 B2 | 4/2016 | Kelly | |
| 9,486,487 B2 | 11/2016 | Cutcliffe | |

FOREIGN PATENT DOCUMENTS

| | | |
|---|---|---|
| CN | 106497791 A | 3/2017 |
| WO | 0207741 A1 | 1/2002 |

(Continued)

OTHER PUBLICATIONS

Takada T, Watanabe K, Makino H, Kushiro A. Reclassification of Eubacterium desmolans as Butyricicoccus desmolans comb. nov., and description of Butyricicoccus faecihominis sp. nov., a butyrate-producing bacterium from human faeces. Int J Syst Evol Microbiol. Oct. 2016;66(10):4125-4131. doi: 10.1099/ijsem.0.001323.*

(Continued)

*Primary Examiner* — Kade Ariani

(57) ABSTRACT

Disclosed herein are probiotic bacterial strains or species that produce short chain fatty acids (SCFA), such as butyrate, and compositions comprising the same. The bacterial strains or compositions prepared thereby are used in preparing food, supplements, compositions, and other consumables to provide health benefits, including therapeutic applications, for a variety of disorders, including metabolic, immune, intestinal, and inflammatory disorders. Thus, also disclosed herein are methods of treating a subject suffering from a disorder, such as a metabolic disorder, an immune disorder, an intestinal disorder, or an inflammatory disorder with a composition comprising the probiotic bacterial strains or species disclosed herein. Uses of a bacterial strain or species and a composition comprising them provided in a nutritional product or medicament to improve health or prevent or treat a variety of disorders in a subject are also disclosed.

20 Claims, 15 Drawing Sheets

Specification includes a Sequence Listing.

(56) References Cited

FOREIGN PATENT DOCUMENTS

| WO | WO-2010124855 A1 * | 11/2010 | ............ A23K 20/10 |
|---|---|---|---|
| WO | WO2016070151 A1 | 5/2016 | |
| WO | WO2016185469 A1 | 11/2016 | |
| WO | 2017160711 A1 | 9/2017 | |
| WO | 2018081550 A1 | 5/2018 | |
| WO | WO2018234645 A1 | 12/2018 | |
| WO | WO2020056298 A1 | 3/2020 | |

OTHER PUBLICATIONS

Sharp R, Macfarlane GT. Chemostat enrichments of human feces with resistant starch are selective for adherent butyrate-producing clostridia at high dilution rates. Appl Environ Microbiol. Oct. 2000;66(10):4212-21. doi: 10.1128/AEM.66.10.4212-4221.2000. PMID: 11010862; PMCID: PMC92288.*

Konstantinidis KT, Ramette A, Tiedje JM. The bacterial species definition in the genomic era. Philos Trans R Soc Lond B Biol Sci. Nov. 29, 2006;361(1475):1929-40. doi: 10.1098/rstb.2006.1920. PMID: 17062412; PMCID: PMC1764935.*

Score, Sequence search results for Seq ID No. 13 in GenCore, 7 pages of PDF.*

Kailasapathy, K., Curr. Issues Intest. Microbiol., 2002, vol. 3, p. 39-48. (Year: 2002).*

Hijova E, Chmelarova A. Short chain fatty acids and colonic health. Bratisl Lek Listy. 2007;108(8):354-8. PMID: 18203540. (Year: 2007).*

UnlockFood.Ca, 2016, 5 pages of pdf. (Year: 2016).*

WO 2016178493 A1, English Translation 15 pages of PDF. (Year: 2016).*

BLAST search for Seq ID No. 7, GenBank EF533982.1, 2 pages of PDF conducted on Nov. 6, 2023. (Year: 2023).*

PCT Search Report and Written Opinion for PCT/US2020/030175 dated Jul. 24, 2020.

Anaerostipes caccae Schwiertz et al., Anaerostipes caccae DSM 14662, Data sheet from DSMZ—German Collection of Microorganisms and Cell Cultures GmbH, URL: https://www.dsmz.de/collection/catalogue/details/culture/DSM-14662, retrieved on Nov. 22, 2022, pp. 4.

Roseburia intestinalis Duncan et al., Roseburia intestinalis DSM 14610, Data sheet from DSMZ—German Colelction of Microorganisms and Cell Cultures GmbH, URL: https://www.dsmz.de/collection/catalogue/details/culture/ DSM-14610, retrieved on Nov. 22, 2022, pp. 4.

Baxter, Nielson T. et al. "Dynamics of Human Gut Microbiota and Short-Chain Fatty Acids in Response to Dietary Interventions with Three Fermentable Fibers", MBIO, vol. 10, No. 1, Jan. 1, 2019, pp. e02566-18.

Bircher, Lea et al. "Effect of cryopreservation and lyophilization on viability and growth of strict anaerobic human gut microbes", Microbial Biotechnology, vol. 11, No. 4, Jul. 1, 2018, pp. 721-733.

Janusz, Michael et al: "Exploiting Mechanism of Action to Develop Next Generation Probiotics", Apr. 1, 2019 Retrieved from the Internet: URL:https://4cau4jsalerlzglkq3wnmjel-wpengine.netdna-ssl.com/wp-content/uploads/2019/04/Janusz-Abstract.pdf; retrieve on Jul. 9, 2020.

Ouwerkerk, D.: "EM_STD:AF316590", Feb. 12, 2001, retrieved from the internet: URL:http://ibis.internal.epo.org/exam/dbfetch.jsp?id-EM_STD:AF316590.

Riviere, Audrey et al: "Bifidobacteria and Butyrate-Producing Colon Bacteria: Importance and Strategies for Their Stimulation in the Human Cut", Frontiers in Microbiology, vol. 7, Jun. 28, 2016.

Zhao Jiajun et al. "Systematic Endocrinology", Popular Science Press, No Known Date, 59 pages.

Third Party Observation for 20730140.9 dated Sep. 15, 2023, 7 pages.

Vital et al., "Revealing the Bacterial Butyrate Synthesis Pathways by Analyzing (Meta)genomic Data", vol. 5, Issue No. 2, Mar./Apr. 2014, 11 pages.

* cited by examiner

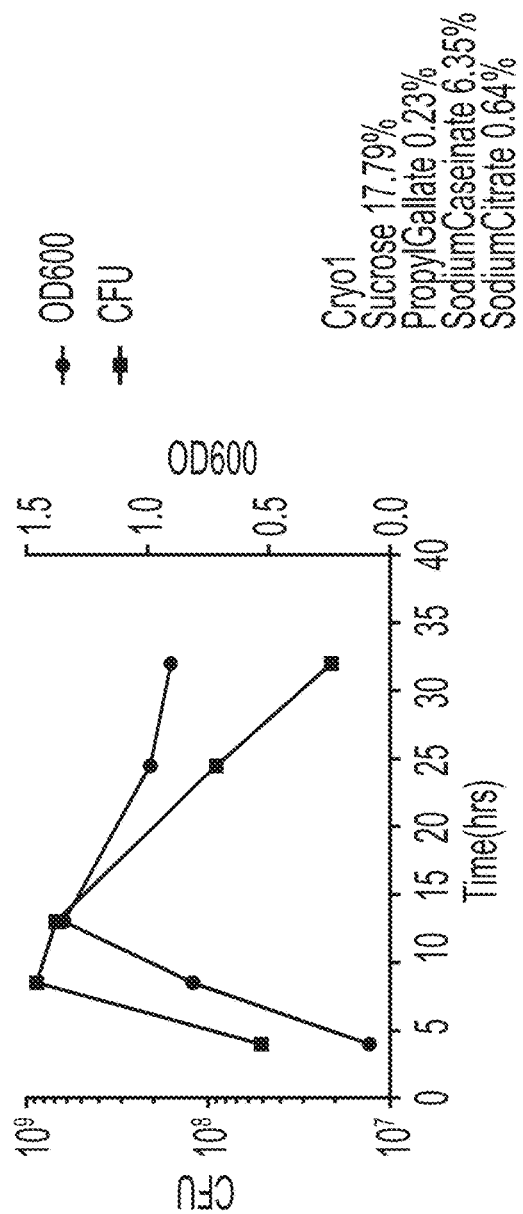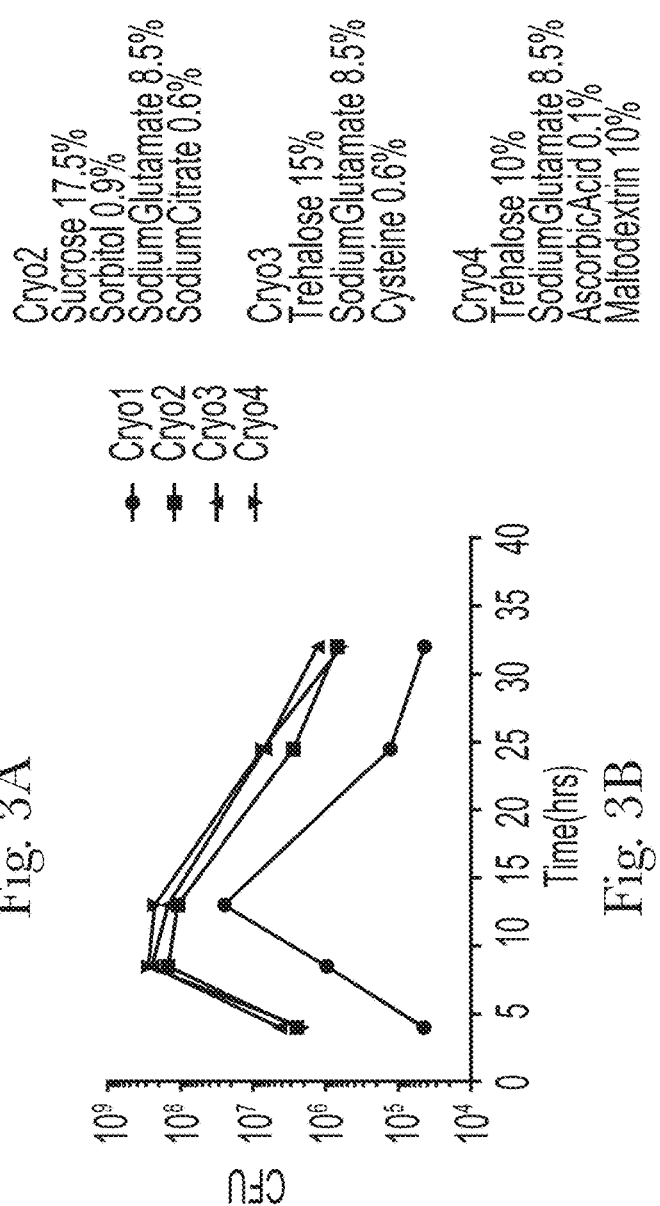
Fig. 3A
Fig. 3B

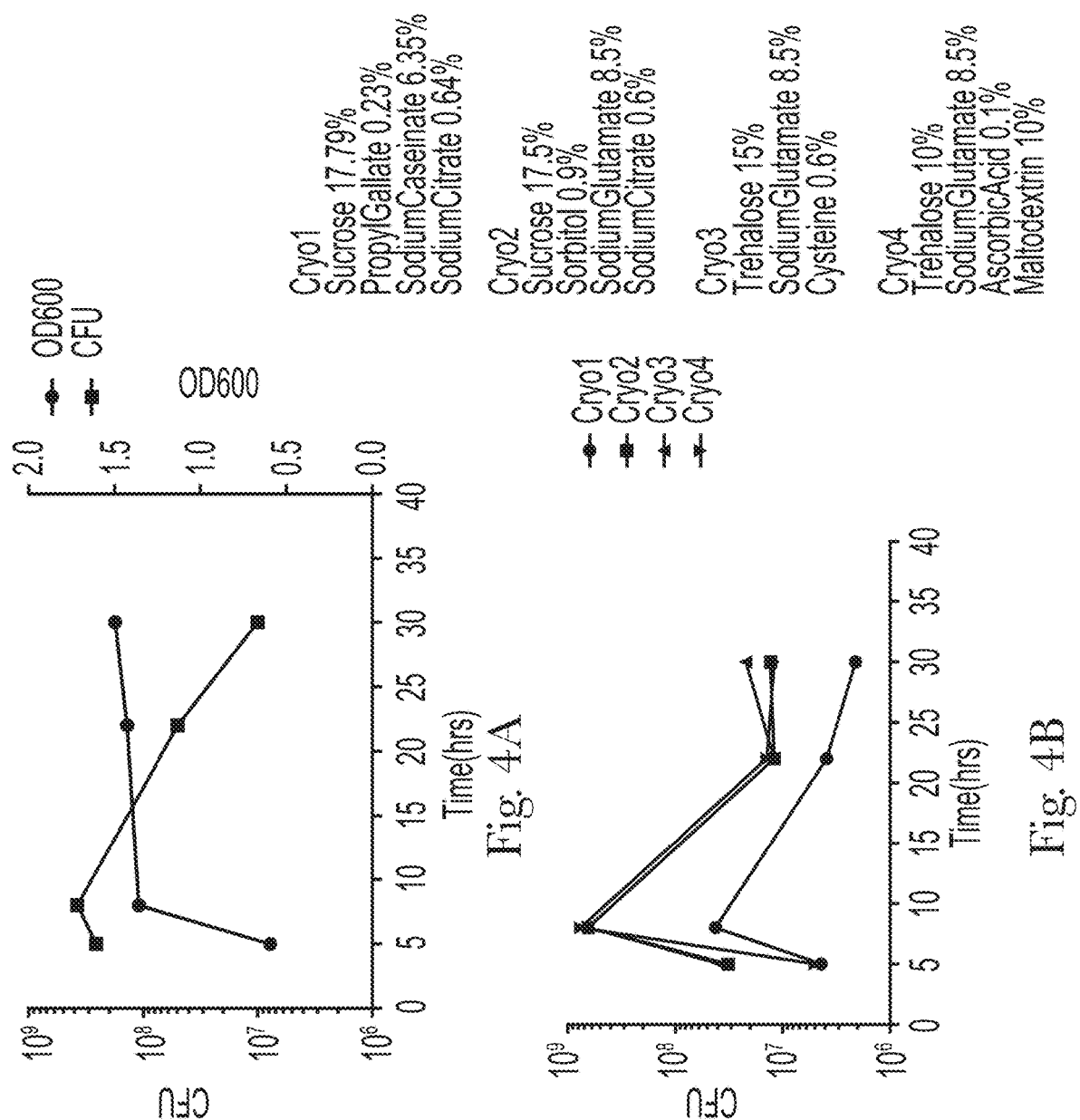

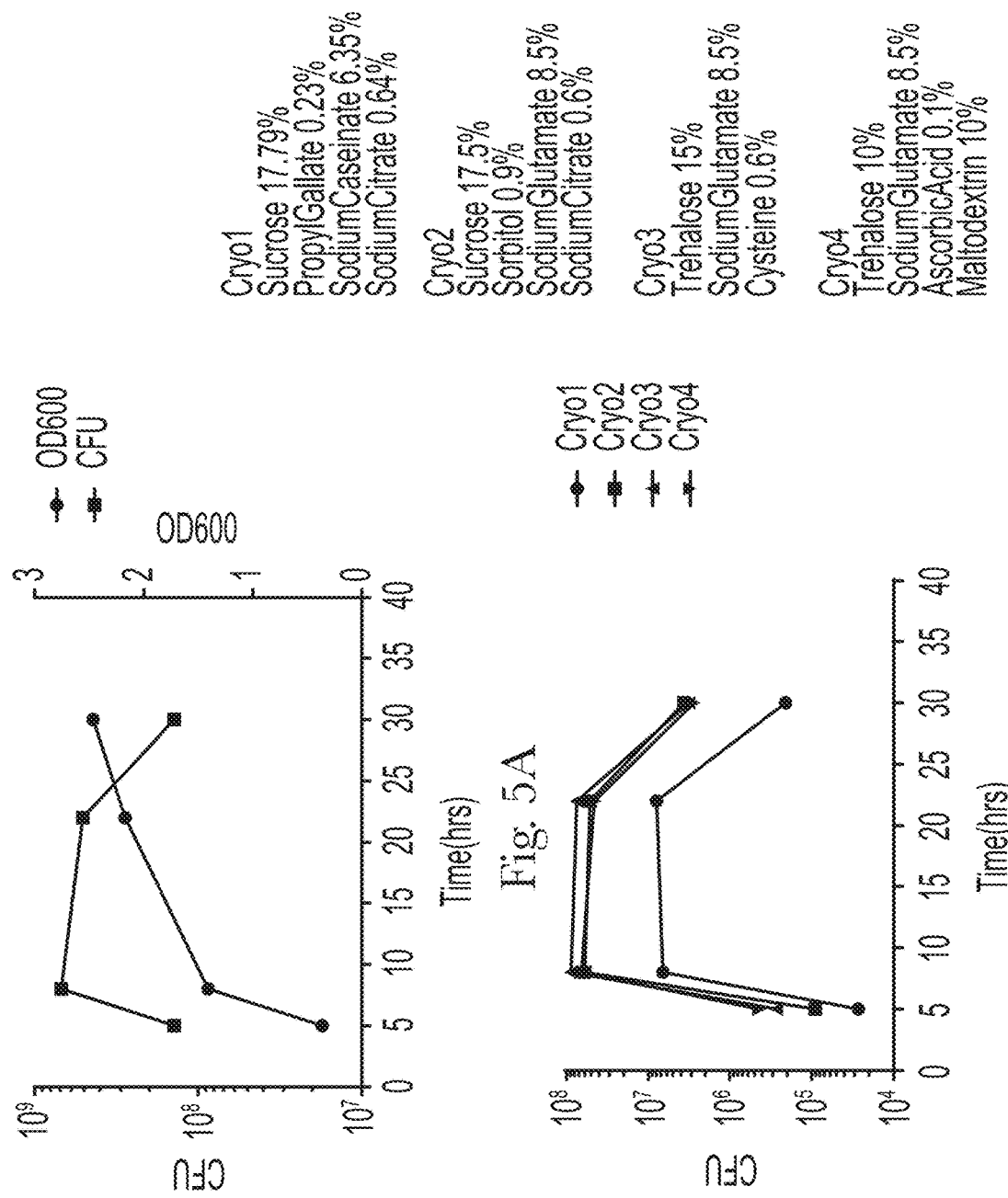

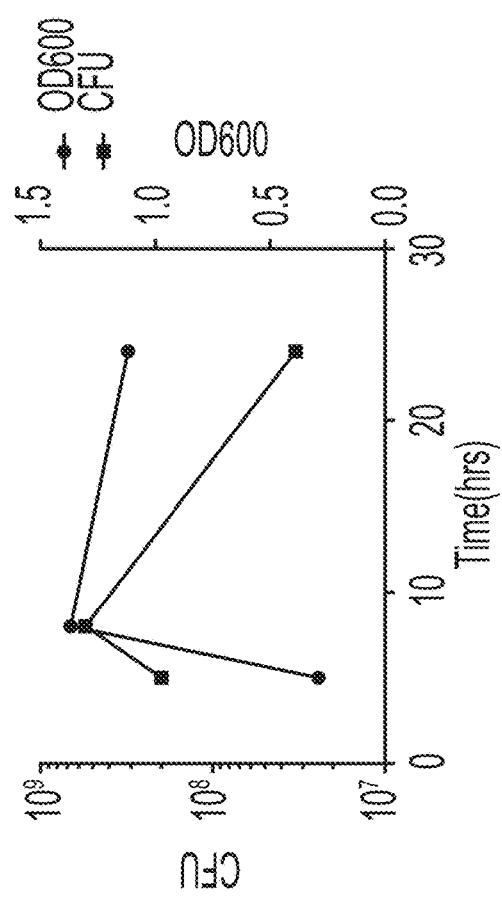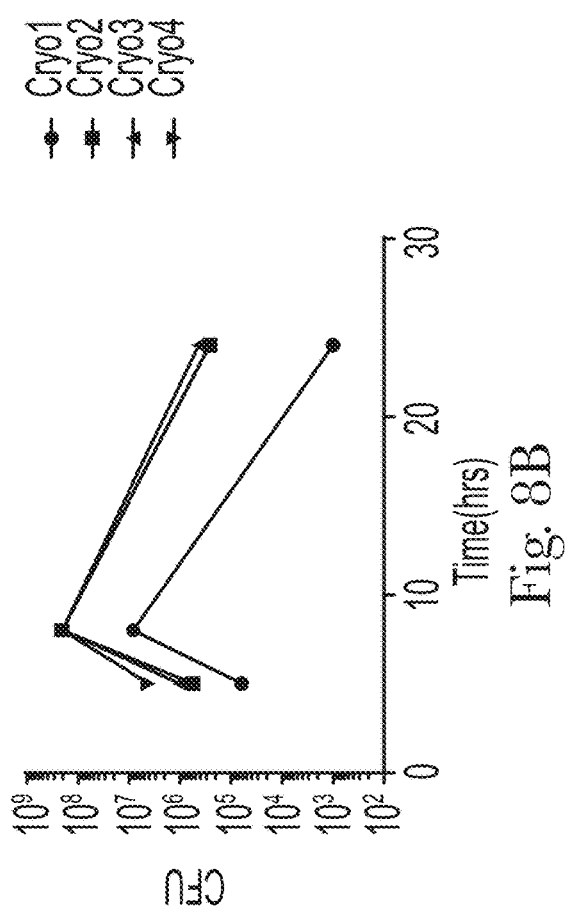

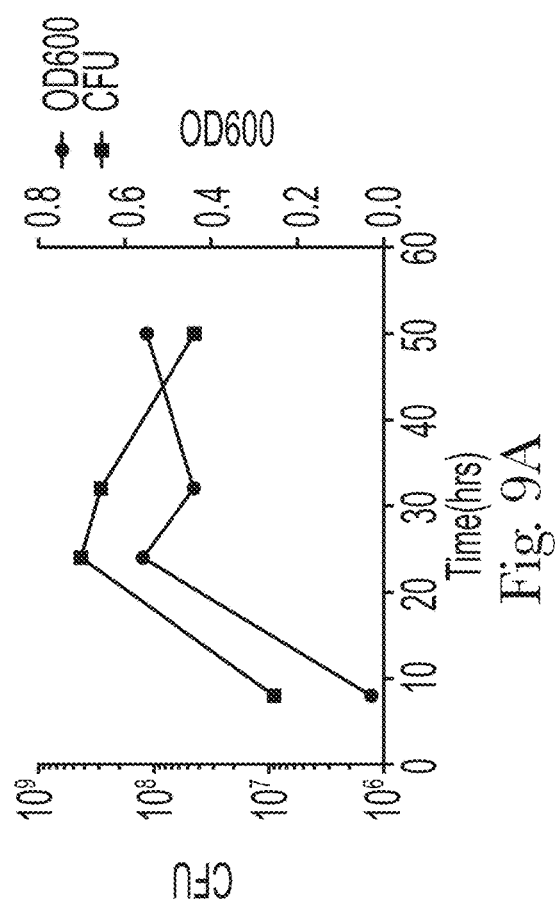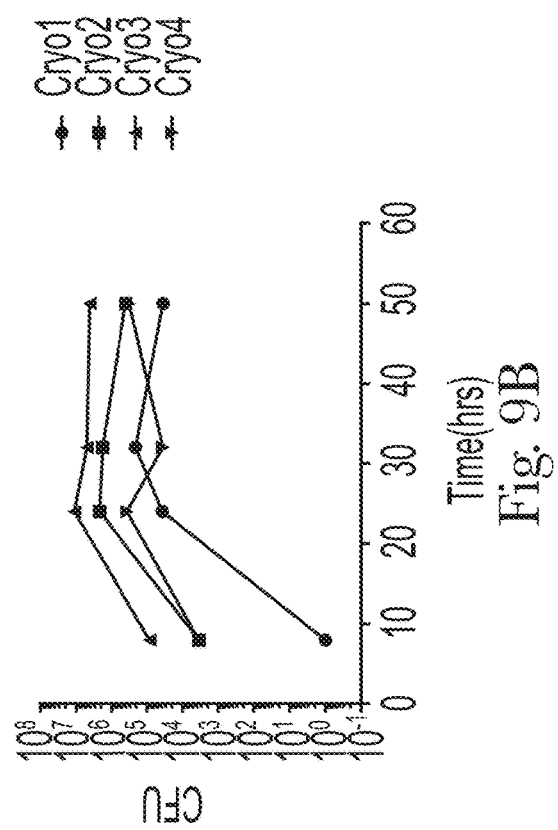

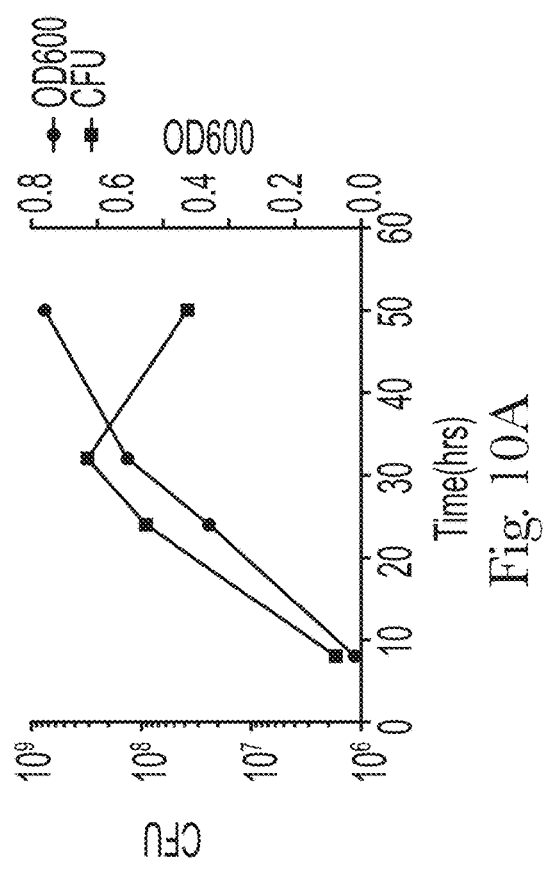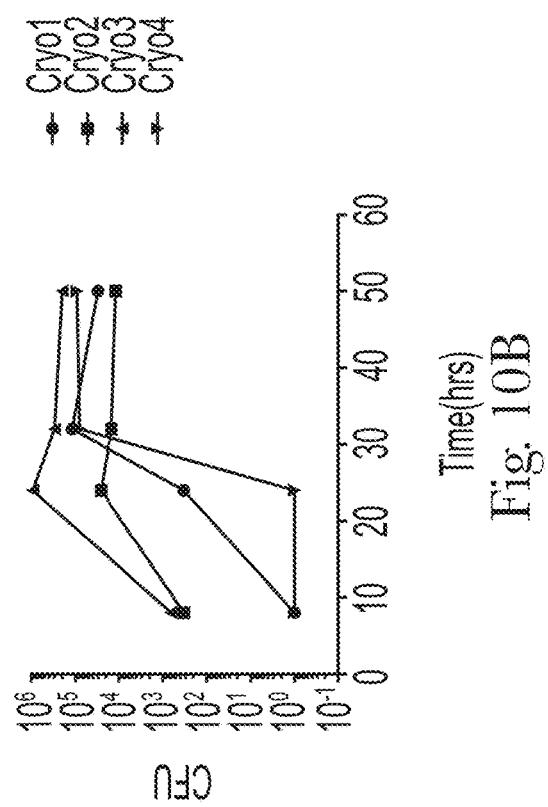
Fig. 10A
Fig. 10B

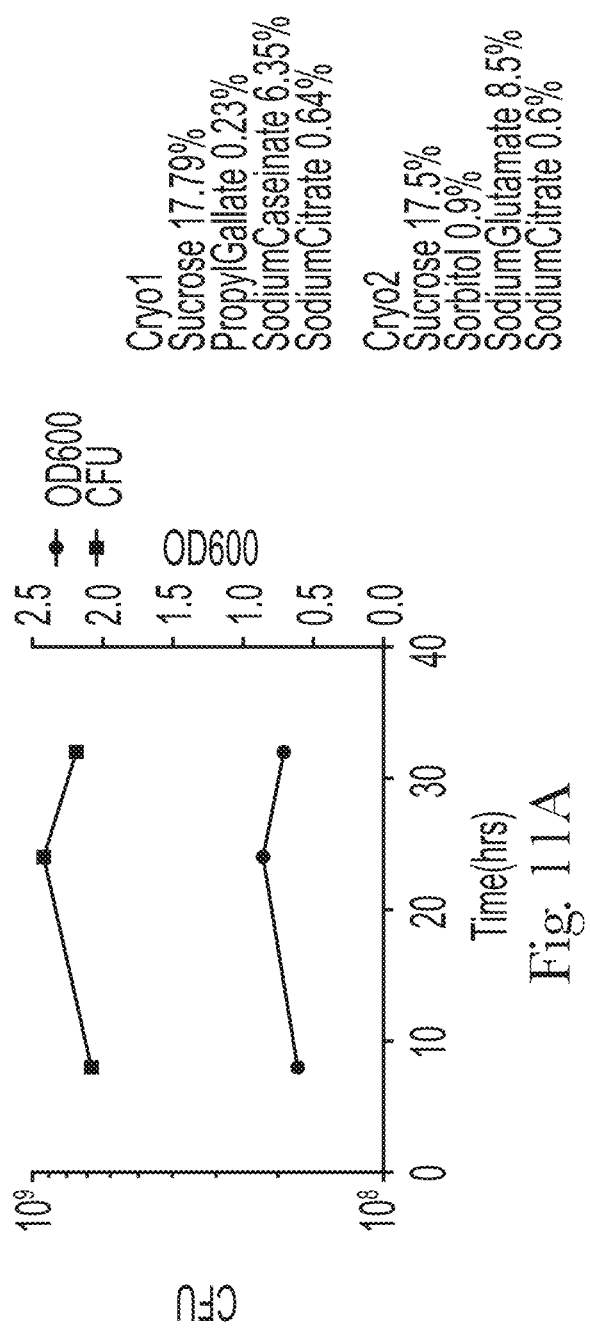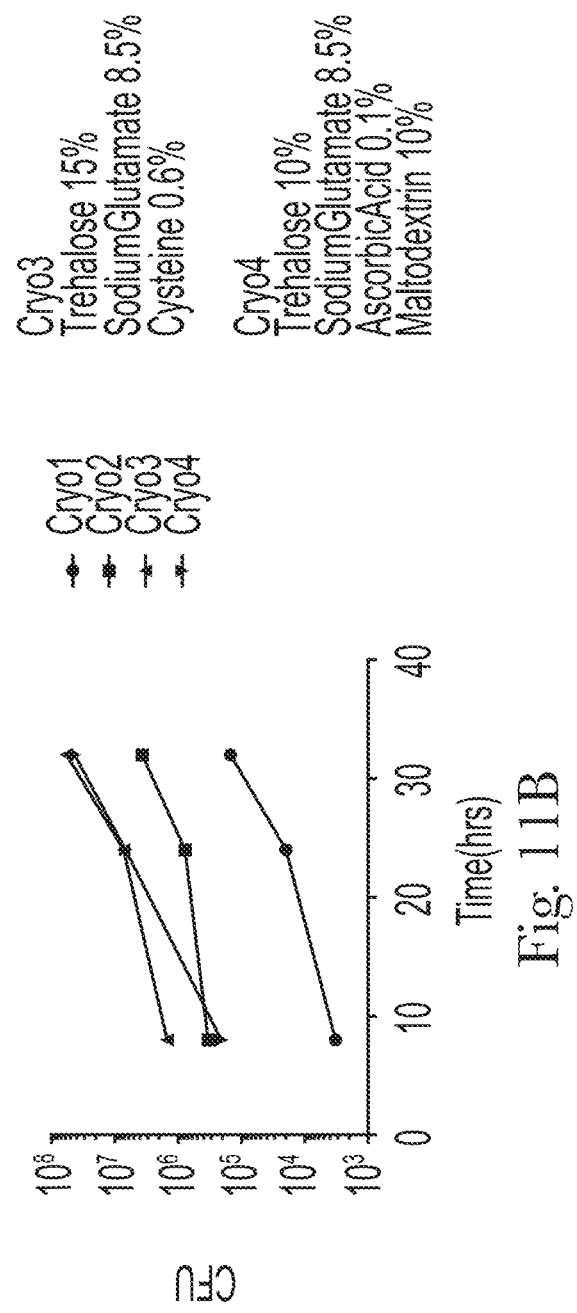
Fig. 11A
Fig. 11B

| Isolate | RCB | TSB | YCFA+RS | PYG | GM-17 | BHI | MTGE |
|---|---|---|---|---|---|---|---|
| Clostridium butyricum YC2-268.2 | ++++ | ++++ | +++++ | +++++ | ++++ | +++ | + |
| Clostridium butyricum YC2-242.3 | ++++ | +++ | +++++ | +++++ | ++++ | ++ | + |
| Clostridium cochlearium YC1-202 | NIZO?? | | | | | | |
| Agathobacter rectalis RC2-6 | +++ | + | +++ | + | + | + | + |
| Agathobacter rectalis YC1-37 | ++++ | +++ | ++++ | +++++ | ++++ | +++ | + |
| Butyricicoccus faecihomonis ODS-26 | ++++ | + | No growth | ++++ | + | + | + |
| Butyricicoccus faecihomonis RC1-135.2 | +++++ | ++ | No growth | +++++ | + | ++ | + |
| Clostridium innocuum M17MSO.2-9 | ++++ | ++ | + | +++ | +++ | +++ | ++ |
| Clostridium Innocuum RC1-219 | ++++ | ++ | No growth | +++ | +++ | +++ | ++ |
| Coprococcus comes RC1-148 | ++++ | ++ | + | +++ | +++ | +++ | ++ |
| Coprococcus comes VDS-14 | +++ | ++ | + | ++++ | ++ | +++ | ++ |
| Roseburia faecis RC1-143 | +++ | No growth | +++++ | +++ | ++ | ++ | ++ |
| Roseburia faecis RC1-78 | +++ | ++ | +++++ | +++ | ++ | + | + |
| anaerostipes hadrus RC2-95 | +++++ | +++ | No growth | +++++ | +++ | +++ | ++ |
| Anaerostipes hadrus FLM9MS-5.1 | +++++ | +++ | No growth | +++++ | ++++ | +++ | +++ |
| Roseburia intestinalis ODS-29 | ++ | + | +++ | + | ++ | + | + |
| Roseburia intestinalis RC1-32 | +++ | No growth | No growth | No growth | No growth | + | No growth |
| Anaerostipes caccae FLM9MS-25 | +++ | + | + | ++++ | ++ | ++ | + |
| Flavonifactor plautii FLM9MS-20 | + | + | + | + | + | + | + |
| Roseburia inulinivorans YC-156 | +++ | No growth | + | + | No growth | + | + |
| Roseburia hominis RC1-32 | +++ | No growth | No growth | No growth | No growth | + | No growth |

Fig. 13

| Isolate | Peak CFU | Time of Peak CFU (Hr) | | | | Log Reduction at Peak CFU (Time 0) | | | | Log Reduction at Peak CFU (Time 30d)[1] | | | |
|---|---|---|---|---|---|---|---|---|---|---|---|---|---|
| | | Cryo 1 | Cryo 2 | Cryo 3 | Cryo 4 | Cryo 1 | Cryo 2 | Cryo 3 | Cryo 4 | Cryo 1 | Cryo 2 | Cryo 3 | Cryo 4 |
| Roseburia faecis RC1-78 | $9.0 \times 10^8$ | 13 | 8.5 | 8.5 | 8.5 | 1.54 | .49 | .77 | .77 | 4.31 | 2.41 | 2.41 | 2.06 |
| Coprococcus comes RC1-148 | $4.0 \times 10^8$ | 8 | 8 | 8 | 8 | 1.96 | .77 | .77 | .77 | 2.54 | .945 | .945 | 1.23 |
| Anaerostipes hadrus FLM9MS-5.1 | $9.0 \times 10^8$ | 8 | 8 | 8 | 8 | 2.01 | 1.02 | .89 | .89 | 2.61 | 2.76 | 2.76 | 2.46 |
| Agathobacter rectalis RC2-6 | $2.0 \times 10^9$ | 22 | 22 | 22 | 22 | 1.48 | .47 | 0.5 | 0.5 | 2.34 | 2.97 | 2.97 | 2.24 |
| Anaerostipes caccae FLM9MS-25 | $4.3 \times 10^8$ | 8 | 8 | 8 | 8 | 1.8 | 0.40 | 0.40 | 0.40 | 2.9 | 0.70 | 0.70 | 1.7 |
| Butyricicoccus faecihominis ODS-26 | $8.0 \times 10^7$ | 8 | 8 | 8 | 8 | 1.92 | 1.10 | 0.89 | 0.89 | 3.49 | 3.05 | 3.05 | 3.07 |
| Roseburia inulinivorans YC1-156 | $6.0 \times 10^6$ | 24 | 24 | 24 | 24 | 3.4 | 4.3 | 3.0 | 3.0 | 5.7 | 2.5 | 2.5 | 3.6 |
| Roseburia intestinalis ODS-29 | $5.0 \times 10^8$ | 32 | 32 | 32 | 32 | 3.70 | 2.31 | 1.11 | 1.11 | 3.32 | 3.5 | 3.5 | 3.53 |
| Flavonifactor plautii FLM9MS-20 | $3.0 \times 10^8$ | 24 | 24 | 24 | 24 | 2.03 | .90 | .70 | .70 | 2.26 | 1.26 | 1.26 | .95 |
| Roseburia hominis RC1-32 | $4.3 \times 10^8$ | 32 | 32 | 32 | 32 | 4.1 | 2.3 | 1.6 | 1.6 | 5.6 | 6.2 | 6.2 | 4.3 |

[1] 30 day stability was done in sealed glass cryo vials in the anaerobic chamber (RT high humidity)

Fig. 14

| Isolate | $O_2$ Sens[1] | Microoxic growth plates[2] |
|---|---|---|
| Clostridium butyricum YC2-268.2 | 60 min | Yes |
| Agathobacter rectalis RC2-6 | 2 min | Few Colonies |
| Butyricicoccus faerihomonis ODS-26 | 5 min | No |
| Clostridium innocuum M17MSO 2.9 | 60 min | Yes |
| Coprococcus comes RC1-148 | 5 min | No |
| Roseburia faecis RC1-78 | 5 min | No |
| Anaerostipes hadrus FLM9MS-5.1 | 5 min | No |
| Roeburia intestinalis ODS-29 | 2 min | No |
| Anaerostipes caccae FLM9MS-25 | 30 min | Yes |
| Flavonifactor plautii FLM9MS-20 | 30 min | No |
| Roseburia inulinivorans YC-156 | 5 min | Few Colonies |
| Roseburia hominis RC1-32 | 2 min | No |

Fig. 15

PROBIOTIC BACTERIAL STRAINS THAT PRODUCE SHORT CHAIN FATTY ACIDS AND COMPOSITIONS COMPRISING SAME

FIELD

The disclosure relates to probiotic bacterial strains or species that produce short chain fatty acids (SCFA), such as butyrate, for their delivery to the colon where SCFA are produced endogenously at their site of action providing health benefits for a variety of disorders, including metabolic, immune, intestinal, and inflammatory disorders, as well as compositions comprising such bacterial strains or species. In certain embodiments, the bacterial strains or compositions are used in preparing food, supplements, and other consumables to provide health benefits, including therapeutic applications, for a variety of disorders, including metabolic, immune, intestinal, and inflammatory disorders.

INCORPORATION BY REFERENCE OF THE SEQUENCE LISTING

This application contains, as a separate part of disclosure, a Sequence Listing in computer-readable form (Filename: 53257_Seqlisting.txt; Size: 60,978,131 bytes; Created: Apr. 24, 2019) which is incorporated by reference herein in its entirety.

BACKGROUND

Obesity and its associated cardiometabolic disorders are a major health care problem and the importance of the gut microbiota and its relationship with cardiometabolic disorders is increasingly being recognized. Increased consumption of dietary fiber has been associated with reduced appetite and weight loss. The gut microbiota ferments non-absorbable dietary fiber and produces short chain fatty acids (SCFA) that are important for intestinal health and metabolic functions (Canfora et al., Nature Reviews Endocrinology 11:577-91, 2015). The health benefits of SCFA, especially butyrate, include maintenance of the gut epithelial barrier by being an energy source for the colonocytes (Ping et al., J. Nutr. 139:1619-25, 2009; Suzuki et al., Br. J. Nutr. 100:297-305, 2008), pathogen inhibition by lowering the local pH (Rios-Covian et al., Frontiers Microbiology 7:1-9, 2016), and increasing mucus production (Jung et al., Nutr. Res. Pract. 9:343-9, 2015). In addition, SCFA have been shown to have anti-inflammatory activity in vitro and in vivo by increasing the number and function of anti-inflammatory T regulatory cells (Smith et al., Science 341:569-73, 2013).

SCFA have been shown to stimulate the production of the enteroendocrine peptides glucagon-like peptide 1 (GLP-1) and peptide YY (PYY), which increase satiety, stimulate the pancreas to secrete insulin, increase energy expenditure and increase central appetite regulation resulting in potential metabolic benefits (Canfora (supra); Yadav et al., J. Biol. Chem. 288:25088-97, 2013; Gao et al., Diabetes 58:1509-17, 2009; Frost et al., Nat. Commun. 5:3611, 2014; Line et al., PLoS ONE 4:e35240, 2012). The obese phenotype and insulin resistance can be transferred by the fecal flora from obese to lean mice (Turnbaugh et al., Nature 444:1027-31, 2006). In humans, a fecal transplant from a lean donor to subjects with metabolic syndrome improves insulin sensitivity and has been associated with an increase in butyrate producing bacteria (Vrieze et al., Gastroenterology 143:913-6, 2012; Kootte et al., Cell Metab. 26:611-9, 2017).

Butyrate levels vary widely among individuals and can be increased by consumption of fermentable fiber (McOrist et al., J. Nutr. 141:883-9, 2011). There are also oral butyrate supplements on the market but, because of the rancid smell of butyrate, the requirement of multiple capsules to deliver an effective dose and its rapid absorption in the upper gastrointestinal tract, this approach is undesirable (Pituch et al., Przeglad Gastroenterologiczny 8:295-8, 2013). Administration of probiotic bacterial strains that produce SCFAs results in the delivery of the butyrate producing organisms to the colon where SCFAs can be produced endogenously at their site of action providing health benefits for a variety of metabolic and immune disorders including, but not limited to, healthy glucose control and weight management.

SUMMARY

The disclosure provides novel probiotic bacterial strains that produce short chain fatty acids (SCFA) that are important for intestinal health and metabolic functions. The disclosure includes a composition comprising at least one human isolate of SCFA-producing bacteria or mixtures thereof, wherein the bacteria comprises a 16S ribosomal RNA (16S-rRNA) encoding gene sequence that is at least about 80% identical to any one of the nucleotide sequences of SEQ ID NOs: 1-23 or a DNA sequence that is at least about 80% identical to any one of the nucleotide sequences of SEQ ID NOs: 24-35, and an excipient, carrier, and/or diluent. In some aspects, the bacteria is selected from the group consisting of *Agathobacter rectalis*, *Anaerostipes caccae*, *Anaerostipes hadrus*, *Butyricicoccus faecihominis*, *Clostridium butyricum*, *Clostridium cochlearium*, *Clostridium innocuum*, *Coprococcus comes*, *Flavonifactor plautii*, *Roseburia faecis*, *Roseburia hominis*, *Roseburia intestinalis*, and *Roseburia inulinivorans*. In some aspects, the bacteria is lyophilized. In some aspects, the excipient is a cryoprotectant. In some aspects, the cryoprotectant comprises a sugar or a sugar alcohol. In some aspects, the cryoprotectant further comprises any one or more of propyl gallate, sodium caseinate, sodium citrate, sodium glutamate, cysteine, ascorbic acid, and/or maltodextrin.

In some aspects, the cryoprotectant comprises sucrose at about 1% to about 25%; trehalose at about 1% to about 25%; sorbitol at about 0.1% to about 5%; propyl gallate at about 0.05% to about 1.0%; sodium caseinate at about 0.5% to about 10%; sodium citrate at about 0.1% to about 5%; sodium glutamate at about 1% to about 15%; cysteine at about 0.01% to about 2.0%; ascorbic acid at about 0.005% to about 5.0%; maltodextrin at about 1% to about 20%; or a combination of any of any one or more of the components as set out above.

In some aspects, the cryoprotectant comprises sucrose at about 15% to about 20%, propyl gallate at about 0.05% to about 1.0%, sodium caseinate at about 4% to about 8%, and sodium citrate at about 0.2% to about 1.0%; sucrose at about 15% to about 20%, sorbitol at about 0.5% to about 1.5%, sodium glutamate at about 5% to about 12%, and sodium citrate at about 0.1% to about 1.5%; trehalose at about 5% to about 20%, sodium glutamate at about 3% to about 15%, cysteine at about 0.01% to about 1.0%; or trehalose at about 5% to about 20%, sodium glutamate at about 3% to about 15%, ascorbic acid at about 0.01% to about 2%, and maltodextrin at about 2% to about 18%.

In some aspects, the cryoprotectant comprises sucrose at about 17.8%, propyl gallate at about 0.2%, sodium caseinate at about 6.4%, and sodium citrate at about 0.6%; sucrose at about 17.5%, sorbitol at about 0.9%, sodium glutamate at about 8.5%, and sodium citrate at about 0.6%; trehalose at about 15%, sodium glutamate at about 8.5%, and cysteine at about 0.1%; or trehalose at about 10%, sodium glutamate at about 8.5%, ascorbic acid at about 0.2%, and maltodextrin at about 10%.

In some aspects, the composition comprises from about 1×E3 to about 1×E11 colony-forming units (CFU) of the SCFA-producing bacteria and mixtures thereof. In some aspects, the bacteria and/or mixtures thereof produce at least about 1000 micromoles of the SCFA over about 24 hours. In some aspects, the SCFA is acetate, propionate, or butyrate, or a combination thereof. In some aspects, the SCFA is butyrate.

In some aspects, the bacteria in the composition survive with less than about a 1 log unit reduction in CFU, less than about a 2 log reduction in CFU, less than about a 3 log reduction in CFU, less than about a 4 log reduction in CFU, less than about a 5 log reduction in CFU, or less than about a 6 log reduction in CFU of viable bacteria over about 12 months after lyophilization in the cryoprotectant.

In some aspects, the composition further comprises a prebiotic and/or a resistant starch.

In some aspects, the composition further comprises at least one additional bacteria that degrades resistant starch. Such additional bacteria include, but are not limited to, *Bifidobacterium adolescentis*, *Ruminococcus bromii*, *Bacteriodes thetaiotamicron*, *Bacteriodes ovatus*, *Bifidobacterium breve*, or *Roseburia intestinalis*.

In some aspects, a composition of the disclosure is a probiotic composition.

The disclosure also provides methods of increasing SCFA in the gastrointestinal tract of a subject comprising administering to the subject an effective amount of any of the compositions disclosed herein. In some aspects, the SCFA is acetate, propionate, or butyrate, or a combination thereof. In some aspects, the SCFA is butyrate. In some aspects, the subject suffers from or is at risk of suffering from a disorder. In some aspects, the disorder is an intestinal disorder, a metabolic disorder, an inflammatory disorder, or an immune disorder. In some aspects, the disorder is insulin resistance, insulin sensitivity, pre-diabetes, diabetes or Type 2 Diabetes Mellitus (T2DM), irritable bowel syndrome, metabolism irregularity, obesity, obesity-related conditions, hypertension, stress, stress-related conditions, drug metabolism irregularity, gastrointestinal infection, Inflammatory Bowel Disease (IBD), or Crohn's Disease.

The disclosure also provides methods for reducing or maintaining glucose level and/or body weight in a subject in need thereof comprising administering to the subject an effective amount of any of the compositions disclosed herein. In some aspects, the subject suffers from diabetes or pre-diabetes.

The disclosure further provides methods for treating, ameliorating, or preventing a disorder in a subject suffering therefrom or at risk of suffering therefrom comprising administering to the subject an effective amount of any of the compositions disclosed herein. In some aspects, the disorder is an intestinal disorder, a metabolic disorder, an inflammatory disorder, or an immune disorder. In some aspects, the disorder is insulin resistance, insulin sensitivity, pre-diabetes, diabetes or T2DM, irritable bowel syndrome, metabolism irregularity, obesity, obesity-related conditions, hypertension, stress, stress-related conditions, drug metabolism, gastrointestinal infection, IBD, or Crohn's Disease.

The disclosure provides uses of a composition as disclosed herein in treating a metabolic disorder, an immune disorder, an intestinal disorder, or an inflammatory disorder, or in the preparation of a medicament or nutritional product for treating a metabolic disorder, an immune disorder, an intestinal disorder, or an inflammatory disorder.

Other features and advantages of the disclosure will become apparent from the following detailed description. It should be understood, however, that the detailed description and the specific examples, while indicating embodiments of the disclosed subject matter, are given by way of illustration only, because various changes and modifications within the spirit and scope of the disclosure will become apparent to those skilled in the art from this detailed description.

BRIEF DESCRIPTION OF THE DRAWING

A more complete understanding of the compositions, methods, and uses disclosed herein can be obtained by reference to the accompanying drawings. These figures are merely schematic representations based on convenience and ease of demonstrating the disclosure, and are, therefore, not intended to define or limit the scope of the exemplary embodiments.

FIGS. 3A-B show the growth curve and post-lyophilization survival for *Roseburia faecis* (RC1-78; i.e., SEQ ID NO: 1). FIG. 3A shows growth curves pre-lyophilization. FIG. 3B shows post-lyophilization survival in four cryoprotectants for each of the pre-lyophilization growth times from FIG. 3A.

FIG. 4A-B show the growth curve and post-lyophilization survival for *Coprococcus comes* (RC1-148, i.e., SEQ ID NO: 10). FIG. 4A shows growth curves pre-lyophilization. FIG. 4B shows post-lyophilization survival in four cryoprotectants for each of the pre-lyophilization growth times from FIG. 4A.

FIG. 5A-B show the growth curve and post-lyophilization survival for *Anaerostipes hadrus* (MS-5.1, i.e., SEQ ID NO: 9). FIG. 5A shows growth curves pre-lyophilization. FIG. 5B shows post-lyophilization survival in four cryoprotectants for each of the pre-lyophilization growth times from FIG. 5A.

FIG. 6A shows growth curves pre-lyophilization. FIG. 6B shows post-lyophilization survival in four cryoprotectants for each of the pre-lyophilization growth times from FIG. 6A.

FIG. 7A shows growth curves pre-lyophilization. FIG. 7B shows post-lyophilization survival in four cryoprotectants for each of the pre-lyophilization growth times from FIG. 7A.

FIG. 8A-B show the growth curve and post-lyophilization survival for *Anaerostipes caccae* (FLM9MS-25, i.e., SEQ ID NO: 15). FIG. 8A shows growth curves pre-lyophilization. FIG. 8B shows post-lyophilization survival in four cryoprotectants for each of the pre-lyophilization growth times from FIG. 8A.

FIG. 9A-B show the growth curve and post-lyophilization survival for *Roseburia hominis* (RC1-32, i.e., SEQ ID NO: 21). FIG. 9A shows growth curves pre-lyophilization. FIG. 9B shows post-lyophilization survival in four cryoprotectants for each of the pre-lyophilization growth times from FIG. 9A.

FIG. 10A-B show the growth curve and post-lyophilization survival for *Roseburia inulinivorans* (YC1-156, i.e., SEQ ID NO: 22). FIG. 10A shows growth curves pre-lyophilization. FIG. 10B shows post-lyophilization survival in four cryoprotectants for each of the pre-lyophilization growth times from FIG. 10A.

FIG. 11A-B show the growth curve and post-lyophilization survival for *Roseburia intestinalis* (ODS-29, i.e., SEQ ID NO: 2). FIG. 11A shows growth curves pre-lyophilization. FIG. 11B shows post-lyophilization survival in four cryoprotectants for each of the pre-lyophilization growth times from FIG. 11A.

FIG. 12A shows growth curves pre-lyophilization. FIG. 12B shows post-lyophilization survival in four cryoprotectants for each of the pre-lyophilization growth times from FIG. 12A.

FIG. 13 shows comparisons of bacterial growth under static conditions in various types of media (1 mL) known in the art (e.g., RCB, TSB, YCFA+RS, PYG, GM-17, BHI, and MTGE) in a deep well plate in the anaerobic chamber at 37° C. (+++++=OD600 of >2; ++++=OD of 1.5-2; +++=OD of 1-1.5; ++=OD of 0.5-1; and +=OD of 0-0.5 at peak) This data shows which media allow the best growth at small scale.

FIG. 14 shows time of peak CFU production during growth phase and bacterial survival for cells harvested at peak CFU after lyophilization using 10 different bacteria in four different cryoprotectants immediately after lyophilization and 30 days after lyophilization.

FIG. 15 shows oxygen sensitivity of various bacterial isolates. For O$_2$Sens[1], bacteria were spotted with a 1:100 dilution of a strain on an RCA plate in an anaerobic chamber, then removed to the air, and then put back into the anaerobic chamber at various time points. Data is expressed as the longest exposure that resulted in visible growth on plates. For Microoxic growth plates[2], plates were spotted with a 1:100 dilution of a strain on an RCA plate in an anoxic chamber (set at 0 oxygen without the oxygen scavenger in the chamber), which kept the oxygen levels at between about 40-160 ppm. Growth was measured by visualization of colonies after about 32 hours.

DETAILED DESCRIPTION

Figure 1:
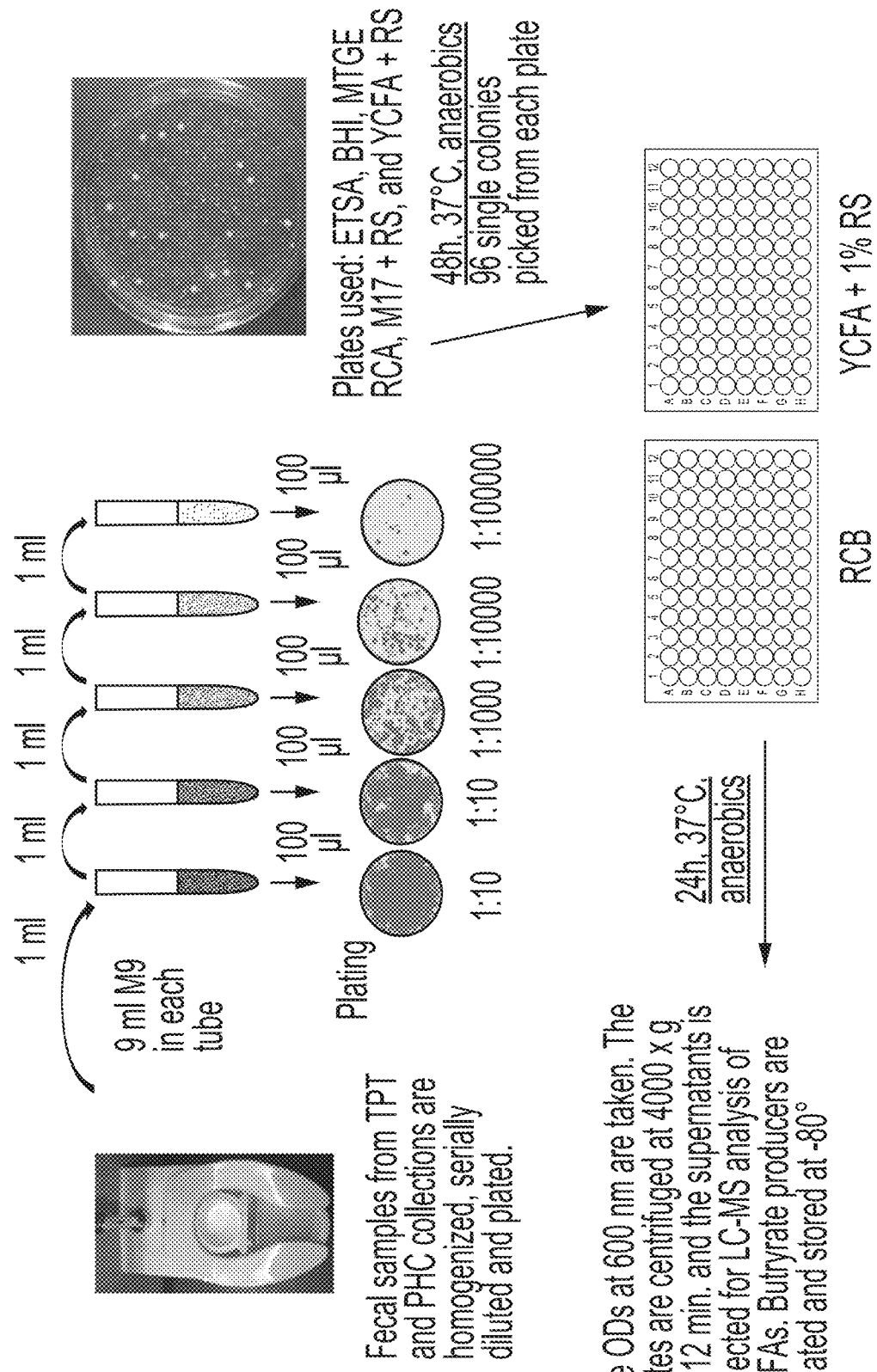
FIG. 1 shows the protocol for isolating, growing, and screening bacteria for production of short chain fatty acids (SCFA)/butyrate.
Figure 2:
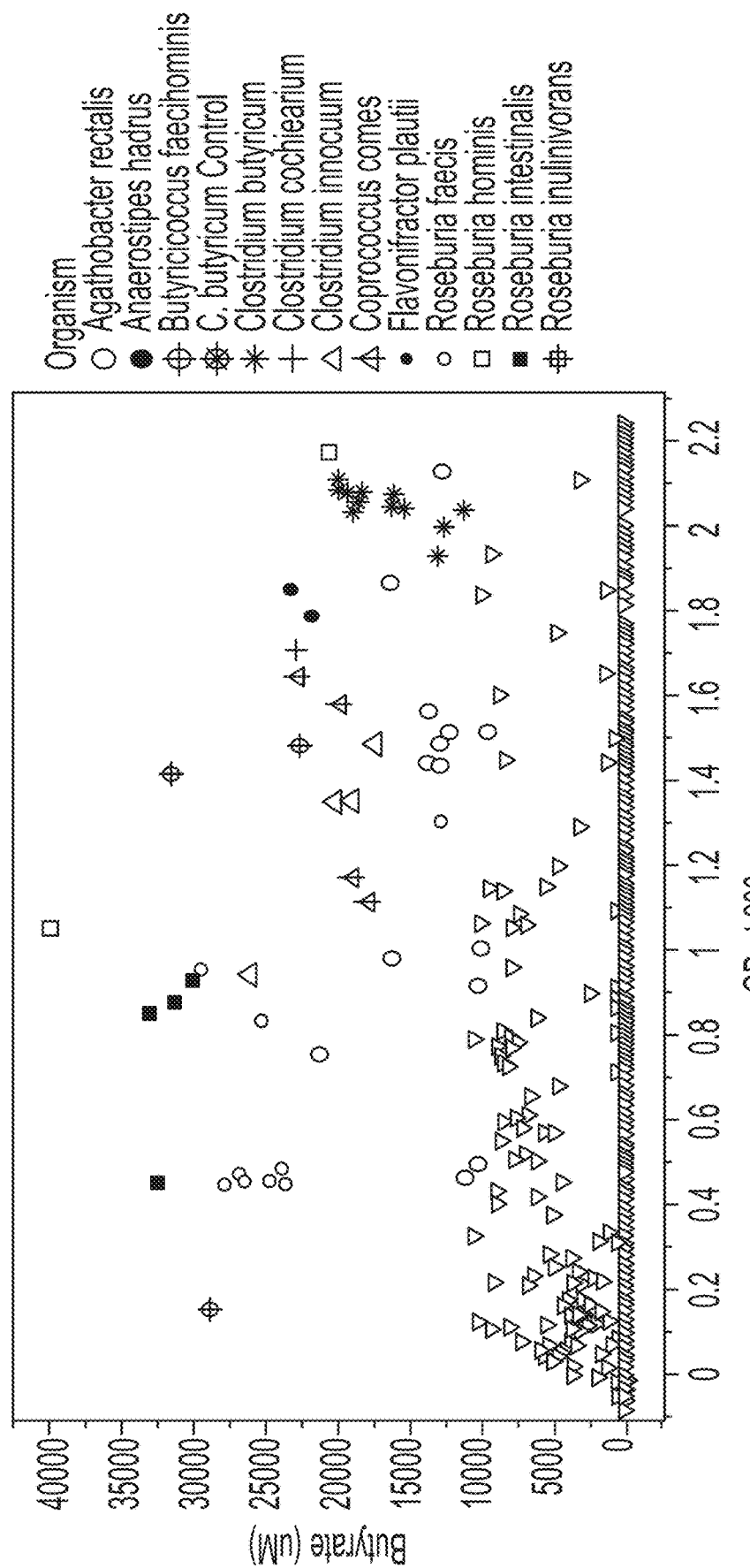
FIG. 2 shows results of screening of bacterial strains for growth and butyrate production on either YCFA or RCB. At least about 1700 bacterial isolates were screened with many showing either no growth or very low butyrate production. The amount of growth (OD 600 nm) is on the x-axis and butyrate production is on the y-axis. The identified bacteria show high butyrate production and diversity of their taxonomy. Dots of the same color represent different isolates.
Figure 6A:
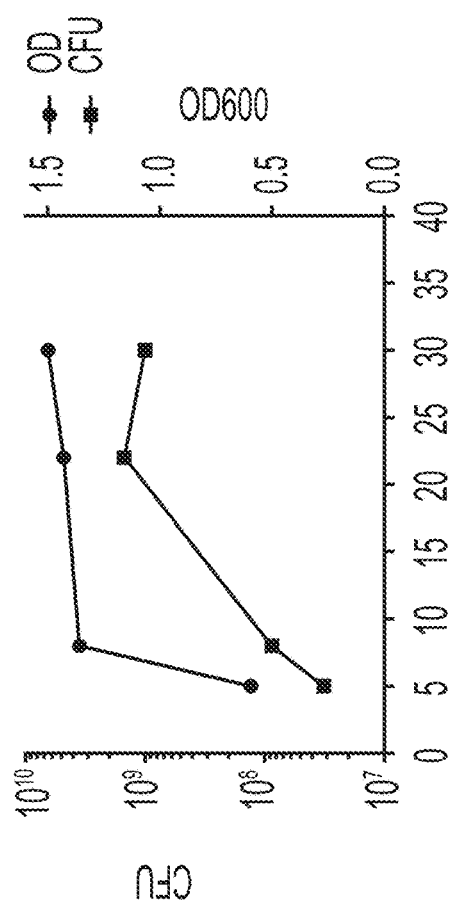
FIG. 6A-B show the growth curve and post-lyophilization survival for *Agathobacter rectalis* (RC2-6, i.e., SEQ ID NO: 11).
Figure 6B:
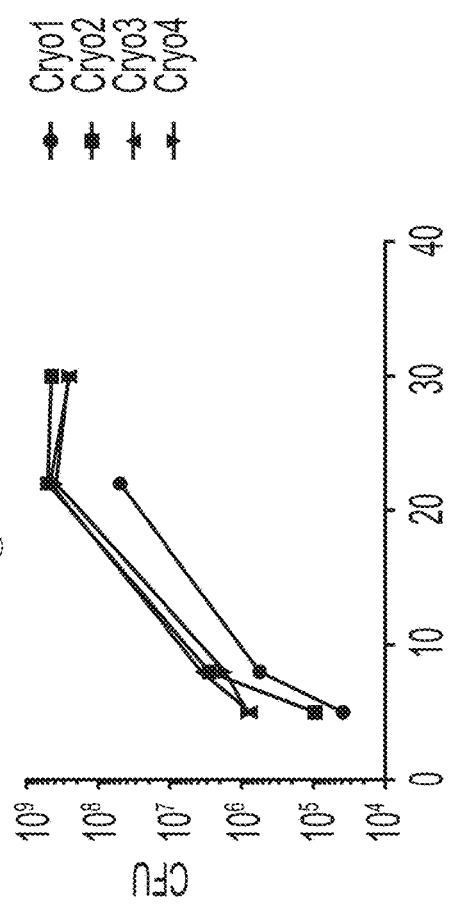
Figure 7A:
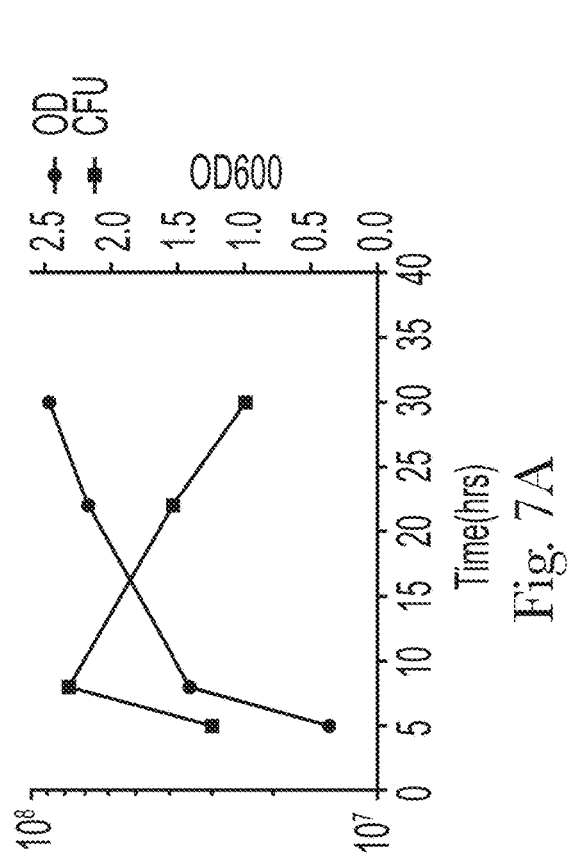
FIG. 7A-B show the growth curve and post-lyophilization survival for *Butyricicoccus faecihominis* (ODS-26, i.e., SEQ ID NO: 13).
Figure 7B:
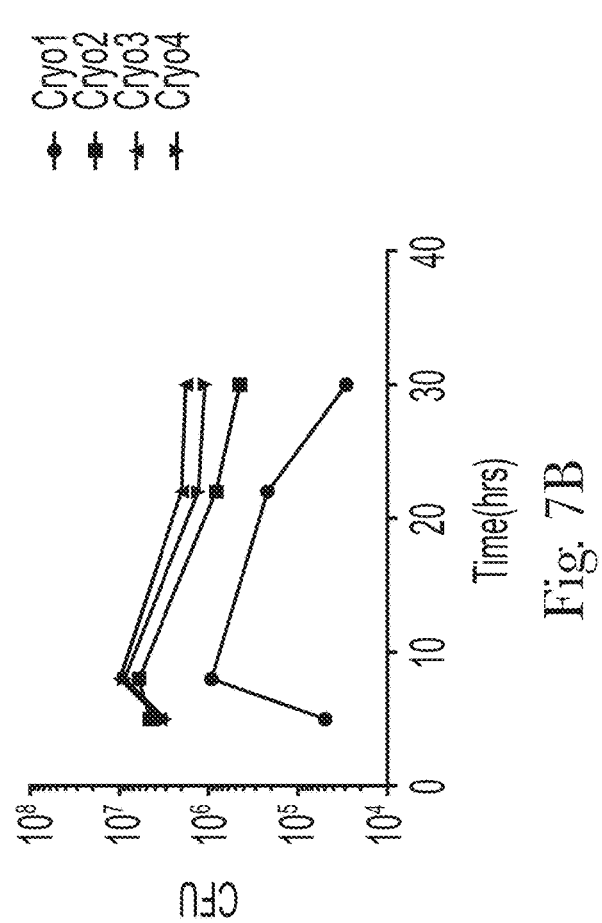
Figure 12A:
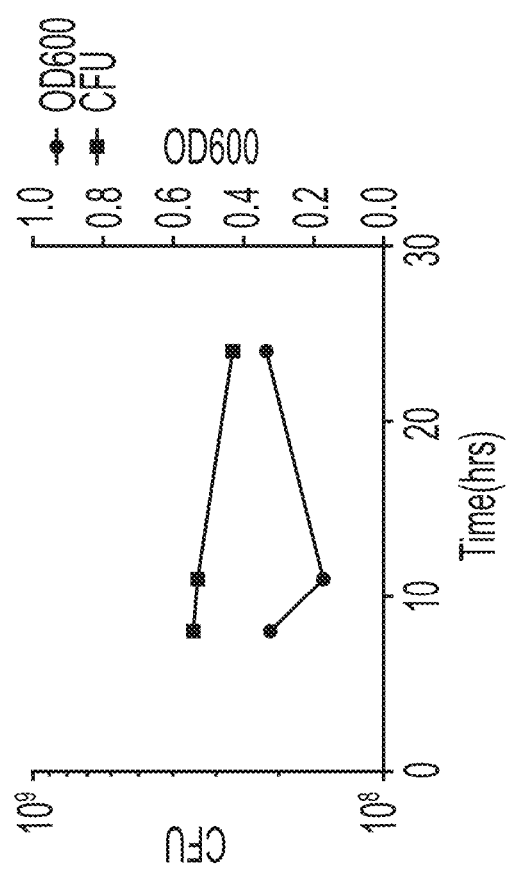
FIG. 12A-B show the growth curve and post-lyophilization survival for *Flavonifactor plautii* (FLM9MS-20, i.e., SEQ ID NO: 19).
Figure 12B:
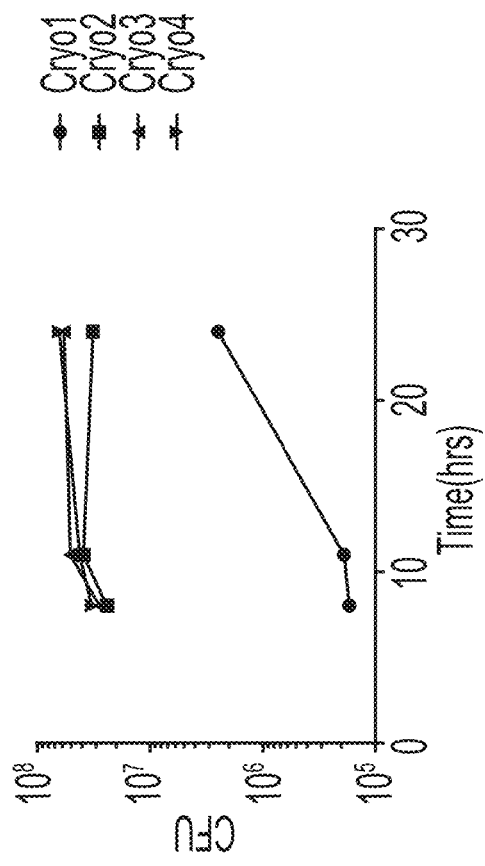

The disclosure provides probiotic bacterial strains or species that produce butyrate and associated compositions comprising the probiotic bacterial strains or species. The disclosed bacterial strains are suitable for delivery to the colon, where short chain fatty acids (SCFA) can be produced endogenously at their site of action, thereby providing health benefits. The health benefits may ease or ameliorate a variety of disorders, including metabolic, immune, intestinal, and inflammatory disorders. In certain embodiments, the bacterial strains or compositions are used in preparing food, supplements, pharmaceutical compositions, and other consumables to providing health benefits, including therapeutic applications, for a variety of disorders, including metabolic, immune, intestinal, and inflammatory disorders.

The terms "microbes" and "microorganisms" are used interchangeably herein to refer to bacteria. The terms "microbiome", "microbiota", and "microbial habitat" are used interchangeably herein and can refer to the ecological community of microorganisms that live on or in a subject's body. Microbiomes can exist on or in many, if not most parts of the subject. Some non-limiting examples of habitats of microbiome can include: body surfaces, body cavities, body fluids, the gut, the colon, skin surfaces and pores, vaginal cavity, umbilical regions, conjunctival regions, intestinal regions, the stomach, the nasal cavities and passages, the gastrointestinal tract, the urogenital tracts, saliva, mucus, and feces.

Bacteria are classified and identified to distinguish one organism from another and to group similar organisms using criteria of interest to microbiologists or other scientists. The bacterial species category defines an organism on the basis of genetic similarity, biochemical, and phenotypic criteria. Within one species, strains and subgroups can differ by the host response they elicit, their environmental habitat, and many other characteristics. A strain designation usually reflects descendants of a single organism and usually are classified based on unique characteristics defined by serotyping, enzyme typing, protein/nucleic acids/plasmid characterization, and functional characteristics important to probiotic strains including, but not limited to, undesirable bacteria inhibition, gastric acid tolerance, adhesion/colonization, hydrophobicity, and immunomodulatory cytokine production. DNA relatedness is used to group strains on the basis of overall genetic similarity.

The term "genome" as used herein, can refer to the entirety of an organism's hereditary information that is encoded in its primary DNA sequence. The genome includes both the genes and the non-coding sequences. For example, the genome, in some aspects, represents a microbial genome. The genetic content of the microbiome can comprise: genomic DNA, RNA, and ribosomal RNA, the epigenome, plasmids, and all other types of genetic information found in the microbes that comprise the microbiome.

In bacteria, the gene that has proven to be the most informative for investigating evolutionary relatedness is a 16S ribosomal RNA (16S-rRNA) encoding gene sequence, a sequence of DNA that encodes the RNA component of the smaller subunit of the bacterial ribosome. The 16S-rRNA encoding gene sequence is highly conserved evolutionarily among species of microorganisms. The 16S-rRNA encoding gene sequence is present in all bacteria, and a related form occurs in all cells, including those of eukaryotes. Consequently, sequencing of the 16S-rRNA subunit can be used to identify and/or compare microorganisms (e.g., bacteria) present in a sample (e.g., a microbiome). 16S-rRNA gene sequencing is a well-established method for studying phylogeny and taxonomy of samples from complex microbiomes or environments that are difficult to study. In various aspects, bacteria are identified by their 16S-rRNA sequence or 16S-rRNA encoding gene sequence.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand. The nucleic acid sequence can be made up of adenine, guanine, cytosine, thymine, and uracil (A, T, C, G, and U) as well as modified versions (e.g. N6-methyladenosine, 5-methylcytosine, etc.). The term "sequencing" as used herein refers to sequencing methods for determining the order of the nucleotide bases—A, T, C, G, and U- in a nucleic acid molecule (e.g., a DNA or RNA nucleic acid molecule). In some aspects of the disclosure, bacteria that produce the greatest levels of SCFA and exhibit tolerance for lyophilization were isolated, and the 16S-rRNA encoding gene sequence from each of these bacteria was sequenced. The 16S-rRNA encoding gene sequences of each of these bacteria (SEQ ID NOs: 1-23) are provided in Table 1.

TABLE 1

16S-rRNA encoding gene sequences of probiotic bacteria of the disclosure

| SEQ ID NO: | Bacteria | Nucleotide sequence |
|---|---|---|
| 1 | RC1-78 2795581 *Roseburia faecis* | TGGAGAGTTTGATCCTGGCTCAGGATGAACGCTGGCGGCGT GCTTAACACATGCAAGTCGAACGAAGCACTCTATTTGATTT YCTTCGGRAWTGAAGATTTTGTGACTGAGTGGCGGACGGG TGAGTAACGCGTGGGTAACCTGCCTCATACAGGGGGATAAC AGTTGGAAACGACTGCTAATACCGCATAAGCGCACAGGAT CGCATGATCYGGTGYGAAAAACTCCGGTGGTATGRGATGG ACCYGCGTCTGATTAGCCAGTTGGCAGGGTAACGGCCTACC AAAGCGACGATCAGTAGCCGACCTGAGAGGGTGACCGCC ACATTGGGACTGAGACACGGCCCAAACTCCTACGGGAGGC AGCAGTGGGGAATATTGCACAATGGGGGAAACCCTGATGC AGCGACGCCGCGTGAGCGAAGAAGTATTTCGGTATGTAAA GCTCTATCAGCAGGGAAGAAGAATGACGGTACCTGACTAA GAAGCACCGGCTAAATACGTGCCAGCAGCCGCGGTA |
| 2 | ODS-29 2795582 *Roseburia intestinalis* | TGGAGAGTTTGATCCTGGCTCAGGATGAACGCTGGCGGCGT GCTTAACACATGCAAGTCGAACGAAGCRCTTTAYTTGATYT CTTCGGARTGAWKRTTTTGTGACTGAGTGGCGGACGGGTGA GTAACGCGTGGGTAACCTGCCTCATACAGGGGGATAACAGT TGGAAACGACTGCTAATACCGCATAAGCGCACAGGGTCRC ATGRCCTGGTGTGAAAAACTCCGGTGGTATGAGATGGACCC GCGTCTGATTAGCCAGTTGGTGGGGTAACGGCCTACCAAAG CGACGATCAGTAGCCGACCTGAGAGGGTGACCGGCCACAT TGGGACTGAGACACGGCCCAAACTCCTACGGGAGGCAGCA GTGGGGAATATTGCACAATGGGGGAAACCCTGATGCAGCG ACGCCGCGTGAGCGAAGAAGTATTTCGGTATGTAAAGCTCT ATCAGCAGGGAAGAAGAAATGACGGTACCTGACTAAGAAG CACCGGCTAAATACGTGCCAGCAGCCGCGGTA |
| 3 | RC2-95 2795583 *Anaerostipes hadrus* | TGGAGAGTTTGATCCTGGCTCAGGATGAACGCTGGCGGCGT GCTTAACACATGCAAGTCGAACGAARCWSCTTAWYTGATY TTCTTCGGAAYTGAHGWTTTGKWGAYTGAGTGGCGGACGG GTGAGTAACGCGTGGGTAACCTRCCCTGTACAGGGGGATAA CAGTCAGAAATGACTGCTAATACYGCATAAGACCACAGCA CCGCATGGTGCAGGGGTAAAARCTCCGGTGGTACAGGATG GACCCGCGTCTGATTAGCTGGTTGGTGAGGTAACGGCTCAC CAAGGCGACGATCAGTAGCCGGCTTGAGAGAGTGAACGGC CACATTGGGACTGAGACACGGCCCAAACTCCTACGGGAGG CAGCAGTGGGGAATATTGCACAATGGGGGAAACCCTGATG CAGCGACGCCGCGTGAGTGAAGAAGTATCTCGGTATGTAA AGCTCTATCAGCAGGGAAGAAAATGACGGTACCTGACTAA GAAGCCCCGGCTAACTACGTGCCAGCAGCCGCGGTA |
| 4 | M17MSO.2-9 2795584 *Clostridium innocuum* | TGGAGAGTTTGATCCTGGCTCAGGATGAACGCTGGCGGCAT GCCTAATACATGCAAGTCGAACGAAGTTTCKAGGAAGCTTG CTTCCAAAGAGACTTAGTGGCGAACGGGTGAGTAACACGT AGGTAACCTGCCCATGTGTCCGGGATAACTGCTGGAAACGG TAGCTAAAACCGGATAGGTATACAGAGCGCATGCTCAGTAT ATTAAAGCGCCCATCAAGGCGTGAACATGGATGGACCTGC GGCGCATTAGCTAGTTGGTGAGGTAACGGCYCACCAAGGC GATGATGCGTAGCCGGCCTGAGAGGGTAAACGGCCACATT GGGACTGAGACACGGCCCAAACTCCTACGGGAGGCAGCAG TAGGGAATTTTCGTCAATGGGGGAAACCCTGAACGAGCAAT GCCGCGTGAGTGAAGAAGGTCTTCGGATCGTAAAGCTCTGT TGTAAGTGAAGAACGGCTCATAGAGGAAATGCTATGGGAG TGACGGTAGCTTACCAGAAAGCCACGGCTAACTACGTGCCA GCAGCCGCGGTA |
| 5 | RC1-219 2795585 *Clostridium innocuum* | TGGAGAGTTTGATCCTGGCTCAGGATGAACGCTGGCGGCAT GCCTAATACATGCAAGTCGAACGAAGTTTCGAGGAAGCTTG CTTCCAAAGAGACTTAGTGGCGAACGGGTGAGTAACACGT AGGTAACCTGCCCATGTGTCCGGGATAACTGCTGGAAACGG TAGCTAAAACCGGATAGGTATACAGAGCGCATGCTCAGTAT ATTAAAGCGCCCATCAAGGCGTGAACATGGATGGACCTGC |

TABLE 1-continued 16S-rRNA encoding gene sequences of probiotic bacteria of the disclosure

| SEQ ID NO: | Bacteria | Nucleotide sequence |
|---|---|---|
|  |  | GGCGCATTAGCTAGTTGGTGAGGTAACGGCCCACCAAGGCR ATGATGCGTAGCCGGCCTGAGAGGGTAAACGGCCACATTG GGACTGAGACACGGCCCAAACTCCTACGGGAGGCAGCAGT AGGGAATTTTCGTCAATGGGGGAAACCCTGAACGAGCAAT GCCGCGTGAGTGAAGAAGGTCTTCGGATCGTAAAGCTCTGT TGTAAGTGAAGAACGGCTCATAGAGGAAATGCTATGGGAG TGACGGTAGCTTACCAGAAAGCCACGGCTAACTACGTGCCA GCAGCCGCGGTA |
| 6 | YC2-268.2 2795588 *Clostridium butyricum* | TGGAGAGTTTGATCCTGGCTCAGGACGAACGCTGGCGGCGT GCTTAACACATGCAAGTCGAGCGATGAAGCTCCTTCGGGAG TGGATTAGCGGCGGACGGGTGAGTAACACGTGGGTAACCT GCCTCATAGAGGGGAATAGCCTTTCGAAAGGAAGATTAAT ACCGCATAAGATTGTAGTACCGCATGGTACAGCAATTAAAG GAGTAATCCGCTATGAGATGGACCCGCGTCGCATTAGCTAG TTGGTGAGGTAACGGCTCACCAAGGCGACGATGCGTAGCC GACCTGAGAGGGTGATCGGCCACATTGGGACTGAGACACG GCCCAGACTCCTACGGGAGGCAGCAGTGGGGAATATTGCA CAATGGGGGAAACCCTGATGCAGCAACGCCGCGTGAGTGA TGACGGTCTTCGGATTGTAAAGCTCTGTCTTTAGGGACGAT AATGACGGTACCTAAGGAGGAAGCCACGGCTAACTACGTG CCAGCAGCCGCGGTA |
| 7 | YC2-242.3 2795590 *Clostridium butyricum* | TGGAGAGTTTGATCCTGGCTCAGGACGAACGCTGGCGGCGT GCTTAACACATGCAAGTCGAGCGATGAAGCTCCTTCGGGAG TGGATTAGCGGCGGACGGGTGAGTAACACGTGGGTAACCT GCCTCATAGAGGGGAATAGCCTTTCGAAAGGAAGATTAAT ACCGCATAAGATTGTAGTACCGCATGGTACAGCAATTAAAG GAGTAATCCGCTATGAGATGGACCCGCGTCGCATTAGCTAG TTGGTGAGGTAACGGCTCACCAAGGCGACGATGCGTAGCC GACCTGAGAGGGTGATCGGCCACATTGGGACTGAGACACG GCCCAGACTCCTACGGGAGGCAGCAGTGGGGAATATTGCA CAATGGGGGAAACCCTGATGCAGCAACGCCGCGTGAGTGA TGACGGTCTTCGGATTGTAAAGCTCTGTCTTTAGGGACGAT AATGACGGTACCTAAGGAGGAAGCCACGGCTAACTACGTG CCAGCAGCCGCGGTA |
| 8 | VDS-14 2795591 *Coprococus comes* | TGGAGAGTTTGATCCTGGCTCAGGATGAACGCTGGCGGCGT GCTTAACACATGCAAGTCGAACGAAGCACTTAWMYYTGAT TCTTCGGATGAAGRKDTTTGTGACTGAGTGGCGGACGGGTG AGTAACGCGTGGGTAACCTGCCTCATACAGGGGGATAACA GTTAGAAATGACTGCTAATACCGCATAAGACCACAGRGYC GCATGRCTYGGTGGGAAAAACTCCGGTGGTATGAGATGGA CCCGCGTCTGATTAGGTAGTTGGTGGGGTAACGGCCTACCA AGCCAACGATCAGTAGCCGACCTGAGAGGGTGACCGGCCA CATTGGGACTGAGACACGGCCCAAACTCCTACGGGAGGCA GCAGTGGGGAATATTGCACAATGGGGGAAACCCTGATGCA GCGACGCCGCGTGAGCGAAGAAGTATTTCGGTATGTAAAG CTCTATCAGCAGGGAAGAAAATGACGGTACCTGACTAAGA AGCACCGGCTAAATACGTGCCAGCAGCCGCGGTA |
| 9 | MS-5.1 2795592 *Anaerostipes hadrus* | TGGAGAGTTTGATCCTGGCTCAGGATGAACGCTGGCGGCGT GCTTAACACATGCAAGTCGAACGAARCWSCTTAWYTGATY TTCTTCGGAAYTGAMGWTTTGKWGAYTGAGTGGCGGACGG GTGAGTAACGCGTGGGTAACCTGCCCTGTACAGGGGGATA ACAGTCAGAAATGACTGCTAATACCGCATAAGACCACAGC ACCGCATGGTGCAGGGGTAAAAACTCCGGTGGTACAGGAT GGACCCGCGTCTGATTAGCTGGTTGGTGAGGTAACGGCTCA CCAAGGCGACGATCAGTAGCCGGCTTGAGAGAGTGAACGG CCACATTGGGACTGAGACACGGCCCAAACTCCTACGGGAG GCAGCAGTGGGGAATATTGCACAATGGGGGAAACCCTGAT GCAGCGACGCCGCGTGAGTGAAGAAGTATCTCGGTATGTA AAGCTCTATCAGCAGGGAAGAAAATGACGGTACCTGACTA AGAAGCCCCGGCTAACTACGTGCCAGCAGCCGCGGTA |
| 10 | RC1-148 2795594 *Coprococus comes* | TGGAGAGTTTGATCCTGGCTCAGGATGAACGCTGGCGGCGT GCTTAACACATGCAAGTCGAACGAAGCACTTWWMYYTGAT TCTTCGGATGAAGRKDTTTGTGACTGAGTGGCGGACGGGTG AGTAACGCGTGGGTAACCTGCCTCRTACAGGGGGATAACA GTTAGAAATGACTGCTAATACCGCATAAGACCACACRGAGCY GCATGGCTCRGTGGGAAAAACTCCGGTGGTATGAGATGGA CCCGCGTCTGATTAGGTAGTTGGTGGGGTAACGGCCTACCA AGCCAACGATCAGTAGCCGACCTGAGAGGGTGACCGGCCA CATTGGGACTGAGACACGGCCCAAACTCCTACGGGAGGCA GCAGTGGGGAATATTGCACAATGGGGGRAACCCTGATGCA |

TABLE 1-continued

16S-rRNA encoding gene sequences of probiotic bacteria of the disclosure

| SEQ ID NO: | Bacteria | Nucleotide sequence |
|---|---|---|
| | | GCGACGCCGCGTGAGCGAAGAAGTATTTCGGTATGTAAAG<br>CTCTATCAGCAGGGAAGAAAATGACGGTACCTGACTAAGA<br>AGCACCGGCTAAATACGTGCCAGCAGCCGCGGTA |
| 11 | RC2-6<br>2795595<br>*Agathobacter rectalis* | TGGAGAGTTTGATCCTGGCTCAGGATGAACGCTGGCGGCGT<br>GCTTAACACATGCAAGTCGAACGAAGCACTTTATTTGATTT<br>CCTTCGGGAYTGATTATTTTGTGACTGAGTGGCGGACGGGT<br>GAGTAACGCGTGGGTAACCTGCCTTGTACAGGGGGATAAC<br>AGTTGGAAACGGCTGCTAATACCGCATAAGCGCACRGCATC<br>GCATGATGCAGTGTGAAAAACTCCGGTGGTATAAGATGGA<br>CCCGCGTTGGATTAGCTAGTTGGTGAGGTAACGGCCCACCA<br>AGGCGACGATCCATAGCCGACCTGAGAGGGTGACCGGCCA<br>CATTGGGACTGAGACACGGCCCAAACTCCTACGGGAGGCA<br>GCAGTGGGGAATATTGCACAATGGGCGAAAGCCTGATGCA<br>GCGACGCCGCGTGAGCGAAGAAGTATTTCGGTATGTAAAG<br>CTCTATCAGCAGGGAAGATAATGACGGTACCTGACTAAGA<br>AGCACCGGCTAAATACGTGCCAGCAGCCGCGGTA |
| 12 | YC1-37<br>2795596<br>*Agathobacter rectalis* | TGGAGAGTTTGATCCTGGCTCAGGATGAACGCTGGCGGCGT<br>GCTTAACACATGCAAGTCGAACGAAGCACTTTATTTGATTT<br>CCTTCGGGACTGATTATTTTGTGACTGAGTGGCGGACGGGT<br>GAGTAACGCGTGGGTAACCTGCCTTGTACAGGGGGATAAC<br>AGTTGGAAACGGCTGCTAATACCGCATAAGCGCACRGCATC<br>GCATGRTGCAGTGTGAAAAACTCCGGTGGTATAAGATGGAC<br>CCGCGTTGGATTAGCTAGTTGGTGAGGTAACGGCCCACCAA<br>GGCGACGATCCATAGCCGACCTGAGAGGGTGACCGGCCAC<br>ATTGGGACTGAGACACGGCCCAAACTCCTACGGGAGGCAG<br>CAGTGGGGAATATTGCACAATGGGCGAAAGCCTGATGCAG<br>CGACGCCGCGTGAGCGAAGAAGTATTTCGGTATGTAAAGCT<br>CTATCAGCAGGGAAGATAATGACGGTACCTGACTAAGAAG<br>CACCGGCTAAATACGTGCCAGCAGCCGCGGTA |
| 13 | ODS-26<br>2795597<br>*Butyricicoccus faecihominis* | TGGAGAGTTTGATCCTGGCTCAGGATGAACGCTGGCGGCGT<br>GCCTAACACATGCAAGTCGAACGGARYYRTTTTGGAAAHY<br>YCTTCGGRRDYGGAATYYTYRRYTTAGTGGCGGACGGGTG<br>AGTAACGCGTGAGCAATCTGCCTTTAAGAGGGGGATAACA<br>GTCGGAAACGGCTGCTAATACCGCATAAAGCATYRAAWYC<br>GCATGWTTTTGATGCCAAAGGAGCAATCCGCTTTTAGATGA<br>GCTCGCGTCTGATTAGCTRGTTGGCGGGGYAACGGCCCACC<br>AAGGCGACGATCAGTAGCCGGACTGAGAGGTTGAACGGCC<br>ACATTGGGACTGAGACACGGCCCAGACTCCTACGGGAGGC<br>AGCAGTGGGGAATATTGCGCAATGGGGGAAACCCTGACGC<br>AGCAACGCCGCGTGATTGAAGAAGGCCTTCGGGTTGTAAA<br>GATCTTTAATCAGGGACGAAACAAATGACGGTACCTGAAG<br>AATAAGCTCCGGCTAACTACGTGCCAGCAGCCGCGGTA |
| 14 | RC-135.2<br>2795598<br>*Butyricicoccus faecihominis* | TGGAGAGTTTGATCCTGGCTCAGGATGAACGCTGGCGGCGT<br>GCCTAACACATGCAAGTCGAACGRARYYRTTTTGGAAAYY<br>YCTTCGGRRRYGGAATHYTYRRYTTAGTGGCGGACGGGTGA<br>GTAACGCGTGAGCAATCTGCCTTTAAGAGGGGGATAACAGT<br>CGGAAACGGCTGCTAATACCGCATAAAGCATYRAAWYCGC<br>ATGWTTTTGATGCCAAAGGAGCAATCCGCTTTTAGATGAGC<br>TCGCGTCTGATTAGCTRGTTGGCGGGGTAACGGCCCACCAA<br>GGCGACGATCAGTAGCCGGACTGAGAGGTTGAACGGCCAC<br>ATTGGGACTGAGACACGGCCCAGACTCCTACGGGAGGCAG<br>CAGTGGGGAATATTGCGCAATGGGGRAACCCTGACGCAG<br>CAACGCCGCGTGATTGAAGAAGGCCTTCGGGTTGTAAAGAT<br>CTTTAATCAGGGACGAAACAAATGACGGTACCTGAAGAAT<br>AAGCTCCGGCTAACTACGTGCCAGCAGCCGCGGTA |
| 15 | MS-25<br>2795599<br>*Anaerostipes caccae* | TGGAGAGTTTGATCCTGGCTCAGGATGAACGCTGGCGGCGT<br>GCTTAACACATGCAAGTCGAACGAAGCATTTAGGATTGAAG<br>TTTTCGGATGGATTTCCTATATGACTGAGTGGCGGACGGGT<br>GAGTAACGCGTGGGGAACCTGCCCTATACAGGGGGATAAC<br>AGCTGGAAACGGCTGCTAATACCGCATAAGCGCACAGAAT<br>CGCATGATTCAGTGTGAAAAGCCCTGGCAGTATAGGATGGT<br>CCCGCGTCTGATTAGCTGGTTGGTGAGGTAACGGCTCACCA<br>AGGCGACGATCAGTAGCCGGCTTGAGAGAGTGAACGGCCA<br>CATTGGGACTGAGACACGGCCCAAACTCCTACGGGAGGCA<br>GCAGTGGGGAATATTGCACAATGGGGGAAACCCTGATGCA<br>GCGACGCCGCGTGAGTGAAGAAGTATTCGGTATGTAAAGC<br>TCTATCAGCAGGGAAGAAAACAGACGGTACCTGACTAAGA<br>AGCCCCGGCTAACTACGTGCCAGCAGCCGCGGTA |

TABLE 1-continued 16S-rRNA encoding gene sequences of probiotic bacteria of the disclosure

| SEQ ID NO: | Bacteria | Nucleotide sequence |
|---|---|---|
| 16 | RC1-364 2795600 *Roseburia intestinalis* | TGGAGAGTTTGATCCTGGCTCAGGATGAACGCTGGCGGCGT GCTTAACACATGCAAGTCGAACGAAGCACTYTAYTTGATYT CTTCGGARTGAWKRTTTTGTGACTGAGTGGCGGACGGGTGA GTAACGCGTGGGTAACCTGCCTCATACAGGGGGATAACAGT TGGAAACGACTGCTAATACCGCATAAGCGCACAGGGTCGC ATGACCTGGTGTGAAAAACTCCGGTGGTATGAGATGGACCC GCGTCTGATTAGCCAGTTGGTGGGGTAACGGCCTACCAAAG CGACGATCAGTAGCCGACCTGAGAGGGTGACCGGCCACAT TGGGACTGAGACACGGCCCAAACTCCTACGGGAGGCAGCA GTGGGGAATATTGCACAATGGGGGAAACCCTGATGCAGCG ACGCCGCGTGAGCGAAGAAGTATTTCGGTATGTAAAGCTCT ATCAGCAGGGAAGAAGAAATGACGGTACCTGACTAAGAAG CACCGGCTAAATACGTGCCAGCAGCCGCGGTA |
| 17 | MS-108 2795601 *Roseburia faecis* | TGGAGAGTTTGATCCTGGCTCAGGATGAACGCTGGCGGCGT GCTTAACACATGCAAGTCGAACGAAGCACTCTATTTGATTT TCTTCGGAAATGAAGATTTTGTGACTGAGTGGCGGACGGGT GAGTAACGCGTGGGTAACCTGCCTCATACAGGGGGATAAC AGTTGGAAACGACTGCTAATACCGCATAAGCGCACAGGAT YGCATGATCCGGTGTGAAAAACTCCGGTGGTATGRGATGGA CCCGCGTCTGATTAGCCAGTTGGCAGGGTAACGGCCTACCA AAGCGACGATCAGTAGCCGACCTGAGAGGGTGACCGGCCA CATTGGGACTGAGACACGGCCCAAACTCCTACGGGAGGCA GCAGTGGGGAATATTGCACAATGGGGGAAACCCTGATGCA GCGACGCCGCGTGAGCGAAGAAGTATTTCGGTATGTAAAG CTCTATCAGCAGGGAAGAAGAATGACGGTACCTGACTAAG AAGCACCGGCTAAATACGTGCCAGCAGCCGCGGTA |
| 18 | YC1-202 2795602 *Clostridium cochlearlum* | TGGAGAGTTTGATCCTGGCTCAGGACGAACGCTGGCGGCGT GCTTAACACATGCAAGTCGAGCGATGAAGCTTCCTTCGGGA AGTGGATTAGCGGCGGACGGGTGAGTAACACGTGGGYAAC CTGCCTCAAAGAGRGGAATAGCCCTCCGAAAGGAGGATTA ATACCGCATAAAGTTAGAGTTTCGCATGAAACTTTAACCAA AGGAGYAATCYGCTTTGAGATGGGCCCGCGTCCCATTAGCT AGTTGGTARGGTAATGGCTTACCAAGGCAACGATGGGTAGC CGACCTGAGAGGGTGATCGGCCACATTGGAACTGAGACAC GGTCCAGACTCCTACGGGAGGCAGCAGTGGGGAATATTGC GCAATGGGGGAAACCCTGACGCAGCAACGCCGCGTGGGTG ATGAAGGTTTTCGGATCGTAAARCCCTGTTTTCTGGGACGA TAATGACGGTACCAGATGAGGAAGCCACGGCTAACTACGT GCCAGCAGCCGCGGTA |
| 19 | MS-20 2795603 *Flavonifractor plautii* | TGGAGAGTTTGATCCTGGCTCAGGATGAACGCTGGCGGCGT GCTTAACACATGCAAGTCGAACGGGGTGCTCATGACGGAG GATTCGTCCAACGGATTGAGTTACCTAGTGGCGGACGGGTG AGTAACGCGTGAGGAACCTGCCTTGGAGAGGGGAATAACA CTCCGAAAGGAGTGCTAATACCGCATGATGCAGTTGGGTCG CATGGCTCTGACTGCCAAAGATTTATCGCTCTGAGATGGCC TCGCGTCTGATTAGCTAGTAGGCGGGGTAACGGCCCACCTA GGCGACGATCAGTAGCCGGACTGAGAGGTTGACCGGCCAC ATTGGGACTGAGACACGGCCCAGACTCCTACGGGAGGCAG CAGTGGGGAATATTGGGCAATGGGCGCAAGCCTGACCCAG CAACGCCGCGTGAAGGAAGAAGGCTTTCGGGTTGTAAACTT CTTTTGTCGGGGACGAAACAAATGACGGTACCCGACGAATA AGCCACGGCTAACTACGTGCCAGCAGCCGCGGTA |
| 20 | MS-70 2795604 *Roseburia faecis* | TGGAGAGTTTGATCCTGGCTCAGGATGAACGCTGGCGGCGT GCTTAACACATGCAAGTCGAACGAAGCACTCTATTTGATTT TCTTCGGAAATGAAGATTTTGTGACTGAGTGGCGGACGGGT GAGTAACGCGTGGGTAACCTGCCTCATACAGGGGGATAAC AGTTGGAAACGACTGCTAATACCGCATAAGCGCACAGGAT YGCATGATCCGGTGTGAAAAACTCCGGTGGTATGRGATGGA CCCGCGTCTGATTAGCCAGTTGGCAGGGTAACGGCCTACCA AAGCGACGATCAGTAGCCGACCTGAGAGGGTGACCGGCCA CATTGGGACTGAGACACGGCCCAAACTCCTACGGGAGGCA GCAGTGGGGAATATTGCACAATGGGGGAAACCCTGATGCA GCGACGCCGCGTGAGCGAAGAAGTATTTCGGTATGTAAAG CTCTATCAGCAGGGAAGAAGAATGACGGTACCTGACTAAG AAGCACCGGCTAAATACGTGCCAGCAGCCGCGGTA |
| 21 | RC1-32 2795605 *Roseburia hominis* | TGGAGAGTTTGATCCTGGCTCAGGATGAACGCTGGCGGCGT GCTTAACACATGCAAGTCGAACGAAGCACTTTAATTGATTT CTTCGGAATGAAGTTTTTGTGACTGAGTGGCGGACGGGTGA GTAACGCGTGGGTAACCTGCCTCATACAGGGGGATAACAGT TGGAAACGACTGCTAATACCGCATAAGCGCACRGGATTGCA |

TABLE 1-continued 16S-rRNA encoding gene sequences of probiotic bacteria of the disclosure

| SEQ ID NO: | Bacteria | Nucleotide sequence |
|---|---|---|
|  |  | TGATCCAGTGTGAAAAACTCCGGTGGTATGAGATGGACCCG<br>CGTCTGATTAGCCAGTTGGCGGGGTAACGGCCCACCAAAGC<br>GACGATCAGTAGCCGACCTGAGAGGGTGACCGGCCACATT<br>GGGACTGAGACACGGCCCAAACTCCTACGGGAGGCAGCAG<br>TGGGGAATATTGCACAATGGGGGAAACCCTGATGCAGCGA<br>CGCCGCGTGAGCGAAGAAGTATTTCGGTATGTAAAGCTCTA<br>TCRGCAGGGAAGAAGAATGACGGTACCTGACTAAGAAGCA<br>CCGGCTAAATACGTGCCAGCAGCCGCGGTA |
| 22 | YC1-156<br>2795607<br>*Roseburia*<br>*inulinivorans* | TGGAGAGTTTGATCCTGGCTCAGGATGAACGCTGGCGGCGT<br>GCTTAACACATGCAAGTCGAACGAAGCACTTTDAYHGATTT<br>CTTCGGAWWGAARTTTTAGTGACTGAGTGGCGGACGGGTG<br>AGTAACGCGTGGGTAACCTGCCTCACACAGGGGGATAACA<br>GWTGGAAACGGCTGCTAATACCGCATAAGCGCACARTACC<br>GCATGGTACAGTGTGAAAAACTCCGGTGGTGTGAGATGGA<br>CCCGCGTCTGATTAGCTAGTTGGCAGGGCARCGGCCTACCA<br>AGGCGACGATCAGTAGCCGACCTGAGAGGGTGACCGGCCA<br>CATTGGGACTGAGACACGGCCCAAACTCCTACGGGAGGCA<br>GCAGTGGGGAATATTGCACAATGGGGGAAACCCTGATGCA<br>GCGACGCCGCGTGAGCGAAGAAGTATTTCGGTATGTAAAG<br>CTCTATCAGCAGGGAAGAAGAAATGACGGTACCTGACTAA<br>GAAGCACCGGCTAAATACGTGCCAGCAGCCGCGGTA |
| 23 | RC1-143<br>2796669<br>*Roseburia*<br>*faecis* | TGGAGAGTTTGATCCTGGCTCAGGATGAACGCTGGCGGCGT<br>GCTTAACACATGCAAGTCGAACGAAGCACTCTATTTGATTT<br>TCTTCGGAAATGAAGATTTTGTGACTGAGTGGCGGACGGGT<br>GAGTAACGCGTGGGTAACCTGCCTCATACAGGGGGATAAC<br>AGTTGGAAACGACTGCTAATACCGCATAAGCGCACAGGAT<br>YGCATGATCYGGTGTGAAAAACTCCGGTGGTATGGGATGG<br>ACCCGCGTCTGATTAGCCAGTTGGCAGGGTAACGGCCTACC<br>AAAGCGACGATCAGTAGCCGACCTGAGAGGGTGACCGGCC<br>ACATTGGGACTGAGACACGGCCCAAACTCCTACGGGAGGC<br>AGCAGTGGGGAATATTGCACAATGGGGGAAACCCTGATGC<br>AGCGACGCCGCGTGAGCGAAGAAGTATTTCGGTATGTAAA<br>GCTCTATCAGCAGGGAAGAAGAATGACGGTACCTGACTAA<br>GAAGCACCGGCTAAATACGTGCCAGCAGCCGCGGTA |

\*R = A or G; Y = C or T; K = G or T; M = A or C; S = G or C; and W = A or T as set out in standard ambiguity codes

TABLE 2

Whole genomic DNA sequences of probiotic bacteria of the disclosure*

| SEQ ID NO: | Bacteria |
|---|---|
| 24 | *Roseburia faecis* |
| 25 | *Roseburia intestinalis* |
| 26 | *Anaerostipes hadrus* |
| 27 | *Clostridium innocuum* |
| 28 | *Clostridium butyricum* |
| 29 | *Coprococcus comes* |
| 30 | *Agathobacter rectalis* |
| 31 | *Butyricicoccus faecihominis* |
| 32 | *Anaerostipes caccae* |
| 33 | *Flavonifractor plautii* |
| 34 | *Roseburia hominis* |
| 35 | *Roseburia inulinivorans* |

*Because of the very large size of these whole genomic sequences for bacteria of the disclosure, these sequences are provided solely in the sequence listing which is part of the disclosure.

In some aspects, bacteria comprise nucleic acid sequences having a particular degree of homology or identity to other bacteria. The terms "identity," "homology," and "homologous" as used herein refer to a degree of complementarity or shared similarity with other nucleotide sequences. There may be partial homology or complete homology (i.e., identical sequences). A nucleotide sequence which is partially complementary, i.e., "substantially homologous" or "substantially identical" to a nucleic acid sequence is one that at least partially inhibits a completely complementary sequence from hybridizing to a target nucleic acid sequence. In some aspects, bacteria of the disclosure comprise a 16S-rRNA encoding gene sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% homologous or identical (100% homologous) to any one of the nucleotide sequences of SEQ ID NOs: 1-23. In some aspects, bacteria of the disclosure comprise a DNA sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% homologous or identical (100% homologous) to any one of the nucleotide sequences of SEQ ID NOs: 24-35. In some aspects, the whole genome sequence of bacteria of the disclosure is found in any one of the nucleotide sequences of SEQ ID NOs: 24-35.

In some aspects, a bacteria comprising the nucleotide sequences of any one of SEQ ID NOs: 1-35 is a probiotic or a probiotic bacteria. As used herein, the term "probiotic" means microbial cell preparations or components of microbial cells with a beneficial effect on the health or well-being of the host. (Salminen et al., Trends Food Sci. Technol. 10 107-10, 1999). The term "probiotic" as used herein can mean one or more microorganisms (e.g., bacteria) which, when administered appropriately, can confer a health benefit on the subject.

Some non-limiting examples of probiotics of the disclosure include, but are not limited to, bacteria, such as *Agathobacter rectalis* (formerly *Eubacterium rectale*), *Akkermansia muciniphila*, *Anaerostipes caccae*, *Anaerostipes hadrus*, *Bifidobacterium adolescentis*, *Bifidobacterium bifidum*, *Bifidobacterium infantis*, *Bifidobacterium longum*, *Butyricicoccus faecihominis*, *Butyrivibrio fibrisolvens*, *Clostridium acetobutylicum*, *Clostridium aminophilum*, *Clostridium beijerinckii*, *Clostridium butyricum*, *Clostridium cochlearium*, *Clostridium colinum*, *Clostridium indolis*, *Clostridium innocuum*, *Clostridium orbiscindens*, *Enterococcus faecium*, *Eubacterium hallii*, *Eubacterium rectale*, *Faecalibacterium prausnitzii*, *Fibrobacter succinogenes*, *Flavonifactor plautii*, *Lactobacillus acidophilus*, *Lactobacillus brevis*, *Lactobacillus bulgaricus*, *Lactobacillus casei*, *Lactobacillus caucasicus*, *Lactobacillus fermentum*, *Lactobacillus helveticus*, *Lactobacillus lactis*, *Lactobacillus plantarum*, *Lactobacillus reuteri*, *Lactobacillus rhamnosus*, *Oscillospira guilliermondii*, *Roseburia cecicola*, *Roseburia faecis*, *Roseburia hominis*, *Roseburia intestinalis*, *Roseburia inulinivorans*, *Ruminococcus flavefaciens*, *Ruminococcus gnavus*, *Ruminococcus obeum*, *Streptococcus cremoris*, *Streptococcus faecium*, *Streptococcus infantis*, *Streptococcus mutans*, *Streptococcus thermophilus*, *Anaerofustis stercorihominis*, *Anaerostipes hadrus*, *Anaerotruncus colihominis*, *Clostridium sporogenes*, *Clostridium tetani*, *Coprococcus*, *Coprococcus comes*, *Coprococcus eutactus*, *Eubacterium cylindroides*, *Eubacterium dolichum*, *Eubacterium ventriosum*, *Roseburia faeccis*, *Roseburia hominis*, *Roseburia intestinalis*, and any combination or mixtures thereof.

In particular aspects, the probiotic is a bacteria including, but not limited to, *Agathobacter rectalis*, *Anaerostipes caccae*, *Anaerostipes hadrus*, *Butyricicoccus faecihominis*, *Clostridium butyricum*, *Clostridium cochlearium*, *Clostridium innocuum*, *Coprococcus comes*, *Flavonifactor plautii*, *Roseburia faecis*, *Roseburia hominis*, *Roseburia intestinalis*, and *Roseburia inulinivorans*, and any combination or mixtures thereof.

As set out above, the bacteria of the disclosure are of interest because of their ability to produce short chain fatty acids (SCFA). In some aspects, bacteria of the disclosure produce at least about 0.5 millimoles (mmol) of the SCFA, at least about 0.6 mmol of the SCFA, at least about 0.7 mmol of the SCFA, at least about 0.8 mmol of the SCFA, at least about 0.9 mmol of the SCFA, at least about 1.0 mmol of the SCFA, at least about 1.2 mmol of the SCFA, at least about 1.4 mmol of the SCFA, at least about 1.6 mmol of the SCFA, at least about 1.8 mmol of the SCFA, at least about 2.0 mmol of the SCFA, at least about 2.2 mmol of the SCFA, at least about 2.4 mmol of the SCFA, at least about 2.6 mmol of the SCFA, at least about 2.8 mmol of the SCFA, at least about 3.0 mmol of the SCFA, at least about 3.2 mmol of the SCFA, at least about 3.4 mmol of the SCFA, at least about 3.6 mmol of the SCFA, at least about 3.8 mmol of the SCFA, at least about 4.0 mmol of the SCFA, at least about 4.2 mmol of the SCFA, at least about 4.4 mmol of the SCFA, at least about 4.4 mmol of the SCFA, at least about 4.6 mmol of the SCFA, at least about 4.8 mmol of the SCFA, at least about 5.0 mmol of the SCFA, at least about 5.5 mmol of the SCFA, at least about 6.0 mmol of the SCFA, at least about 6.5 mmol of the SCFA, at least about 7.0 mmol of the SCFA, at least about 7.5 mmol of the SCFA, at least about 8.0 mmol of the SCFA, at least about 8.5 mmol of the SCFA, at least about 9.0 mmol of the SCFA, at least about 9.5 mmol of the SCFA, at least about 10 mmol of the SCFA, at least about 11 mmol of the SCFA, at least about 12 mmol of the SCFA, at least about 13 mmol of the SCFA, at least about 14 mmol of the SCFA, at least about 15 mmol of the SCFA, at least about 16 mmol of the SCFA, at least about 17 mmol of the SCFA, at least about 18 mmol of the SCFA, at least about 19 mmol of the SCFA, at least about 20 mmol of the SCFA, at least about 25 mmol of the SCFA, at least about 30 mmol of the SCFA, at least about 35 mmol of the SCFA, at least about 40 mmol of the SCFA, at least about 45 mmol of the SCFA, at least about 50 mmol of the SCFA, at least about 55 mmol of the SCFA, at least about 60 mmol of the SCFA, at least about 65 mmol of the SCFA, at least about 70 mmol of the SCFA, at least about 75 mmol of the SCFA, at least about 80 mmol of the SCFA, at least about 85 mmol of the SCFA, at least about 90 mmol of the SCFA, at least about 95 mmol of the SCFA, at least about 100 mmol of the SCFA, at least about 110 mmol of the SCFA, at least about 120 mmol of the SCFA, at least about 130 mmol of the SCFA, at least about 140 mmol of the SCFA, at least about 150 mmol of the SCFA, at least about 160 mmol of the SCFA, at least about 170 mmol of the SCFA, at least about 180 mmol of the SCFA, at least about 190 mmol of the SCFA, at least about 200 mmol of the SCFA, at least about 250 mmol of the SCFA, or at least about 300 mmol of the SCFA over a period of about 24 hours.

In some aspects, SCFA production ranges from about 1 millimole over about 24 hours to about 300 millimoles over about 24 hours. In some aspects, SCFA production ranges from about 1 millimole over about 24 hours to about 100 millimoles over about 24 hours. In some aspects, SCFA production ranges from about 1 millimole over about 24 hours to about 50 millimoles over about 24 hours. In some aspects, SCFA production ranges from about 4 millimoles over about 24 hours to about 40 millimoles over about 24 hours.

In some aspects, such amount or concentration of SCFA is measured over a period of time which varies from about 24 hours. For example, in some aspects, the SCFA production is measured over a period of about 12 hours, over a period of about 36 hours, over a period of about 2 days, over a period of about 3 days, over a period of about 4 days, over a period of about 5 days, over a period of about 6 days, over a period of about a week, and the like. In those aspects, the amount of SCFA production, therefore, will be greater or lesser than what is disclosed herein for a period of about 24 hours. In particular aspects, the SCFA is measured over a period of about 24 hours.

In various aspects, the SCFA is acetate, butyrate, or propionate, or combinations thereof. In particular aspects, the SCFA is butyrate. Thus, in some more particular aspects, the production of butyrate is measured over a period of about 24 hours.

As described herein, SCFA are known to be important for intestinal health and metabolic functions. The health benefits of SCFA, especially butyrate, include, but are not limited to, anti-inflammatory activity, maintenance of the gut epithelial barrier, pathogen inhibition by lowering the local pH, and increasing mucus production. In various aspects, the SCFA produced by the bacteria include, but are not limited to, acetic acid, prop-ionic acid, butyric (i.e., butanoic) acid, isobutyric (i.e., isobutanoic) acid, valeric (i.e., pentanoic) acid, or isovaleric (i.e., isopentanoic) acid, or combinations thereof, often referred to by their conjugate bases, e.g, acetate, propionate, butyrate (i.e., butanoate), isobutyrate (i.e., isobutanoate), valerate (i.e., pentanoate), isovalerate (i.e., isopentanoate), or combinations thereof. In some aspects, the SCFA produced by the bacteria is butyrate.

Thus, the disclosure includes bacteria that modulate or increase butyrate production. In the colon, dietary fiber can be processed by butyrate-producing microorganisms to produce butyrate (i.e., butanoate). In turn, butyrate can initiate G-protein coupled receptor (GPCR) signaling, leading to glucagon-like peptide-1 (GLP-1) secretion which can result in increased insulin sensitivity and/or decreased appetite. By altering the butyrate-producing microbiome in a subject, the pathway responsible for insulin sensitivity can be stimulated. In some subjects, insulin sensitivity can be increased and/or restored to pre-diabetic levels with a microbial composition.

In some aspects, the bacteria of the disclosure is provided in a composition (i.e., a probiotic composition). In some aspects, various types of bacteria of the disclosure are combined in the composition. In particular aspects, the composition comprises at least one human isolate of SCFA-producing bacteria or mixtures thereof, wherein the bacteria comprises a 16S-rRNA encoding gene sequence that is at least about 80% identical to any one of the nucleotide sequences of SEQ ID NOs: 1-23, or a whole genome DNA sequence that is at least about 80% identical to any one of the nucleotide sequences of SEQ ID NOs: 24-35, and an excipient, carrier, and/or diluent. In various aspects, the mixture is any two or more bacteria. Thus, the mixture may comprise three or more, four or more, five or more, six or more, seven or more, eight or more, nine or more, ten or more, and the like. This composition may be in the form of a nutritional supplement or a pharmaceutical composition. In some aspects, one or more of the bacteria species or strains described herein are used to create a formulation comprising an effective amount of the composition for treating a subject. In some aspects, the effective amount is an amount effective to provide a health benefit to a subject. In some aspects, the effective amount is a therapeutically effective amount. The composition can be in any formulation known in the art. Some non-limiting examples can include topical, capsule, pill or tablet, lozenge, sachet, enema, gel, liquid, bulk powder for reconstitution or a drink prepared from bulk powder, and the like.

In various aspects, the composition comprises one or more strains or species of metabolically active, i.e., live and/or lyophilized, or non-viable, heat-killed, irradiated, or lysed probiotic bacteria, as described herein, and a physiologically, pharmaceutically, or nutritionally acceptable excipient, carrier or diluent. In some aspects, the one or more species or strains disclosed herein may be included in a food or beverage product, cosmetic, or nutritional supplement.

Nutritionally acceptable excipients, carriers or diluents include, but are not limited to, those suitable for human or animal consumption and those that are used standardly in the food or supplement industry. Typical nutritionally acceptable excipients, carriers or diluents are familiar to the skilled person in the art.

Examples of such suitable excipients for the various different compositions described herein, in some aspects, are found in the "Handbook of Pharmaceutical Excipients, 2nd Edition, (1994), Edited by A Wade and P J Weller. Acceptable carriers or diluents, in some aspects, are described, for example, in Remington's Pharmaceutical Sciences, Mack Publishing Co. (A. R. Gennaro edit. 1985). Such suitable carriers include, but are not limited to, lactose, starch, glucose, cellulose, microcrystalline cellulose, methyl cellulose, magnesium stearate, mannitol, sorbitol and the like. Such suitable diluents include, but are not limited to water, ethanol, propylene glycol, and glycerol.

In some aspects, a suitable excipient is a stabilizing excipient or cryoprotectant, which preserves viability of the bacteria. In various aspects, the terms "stabilizing excipient" and "cryoprotectant" are used interchangeably herein. In some aspects, such cryoprotectant preserves viability of the bacteria after it is lyophilized. In some aspects, a suitable cryoprotectant includes inositol, sorbitol, mannitol, trehalose, glucose, sucrose, corn syrup, DMSO, starches and/or modified starches of all types, PVP, maltose, or other mono and disaccharides. In some aspects, an effective amount of a cryoprotectant is used to minimize cell damage on freezing.

In some aspects, the cryoprotectant keeps the bacteria viable for an extended period of time. In some aspects, the bacteria survive with less than about a 1 log unit reduction in CFU, less than about a 2 log reduction in CFU, less than about a 3 log reduction in CFU, less than about a 4 log reduction in CFU, less than about a 5 log reduction in CFU, or less than about a 6 log reduction in CFU of viable bacteria over about 12 months after lyophilization in the cryoprotectant.

In various aspects, the cryoprotectant comprises a carbohydrate. In various aspects, the carbohydrate is a sugar. In some aspects, the sugar does not crystallize. In some aspects, the sugar is a monosaccharide or disaccharide including, but not limited to, sucrose, trehalose, glucose, galactose, lactose, maltose, mannose, or a sugar alcohol including, but not limited to, ethylene glycol, glycerol, erythritol, threitol, arabitol, sorbitol, mannitol, xylitol, ribitol, galactitol, fucitol, iditol, inositol, volemitol, isomalt, maltitol, lactitol, maltotritol, maltotetraitol, polyglycitol, or alonitol, or a polysaccharide (such as maltodextrin and inulin) or any combination or mixture thereof. In some aspects, the sugar or sugar alcohol is present at about 0.1% to about 25%. In some aspects, the sugar is present at about 0.1%, at about 0.2%, at about 0.3%, at about 0.4%, at about 0.5%, at about 0.6%, at about 0.7%, at about 0.8%, at about 0.9%, at about 1%, at about 2%, at about 3%, at about 4%, at about 5%, at about 6%, at about 7%, at about 8%, at about 9%, at about 10%, at about 11%, at about 12%, at about 13%, at about 14%, at about 15%, at about 16%, at about 17%, at about 18%, at about 19%, at about 20%, at about 21%, at about 22%, at about 23%, at about 24%, or at about 25%. In some aspects, the sugar is sucrose. In some aspects, the sucrose is present at about 15% to about 20%, or at about 18%, or at about 17.8%. In some aspects, the sugar is trehalose. In some aspects, the trehalose is present at about 5% to about 20%, or at about 10%. In some aspects, the sugar alcohol is sorbitol. In some aspects, sorbitol is present in the cryoprotectant at about 0.1% to about 5%. In some aspects, sorbitol is present at about 0.5% to about 1.5%.

In various aspects, the cryoprotectant comprises sodium citrate. In some aspects, the cryoprotectant comprises a sugar or sugar alcohol and sodium citrate. In some aspects, the sodium citrate is present in the cryoprotectant at about 0.1% to about 5.0%. In some aspects, the sodium citrate is present in the cryoprotectant at about 0.1%, at about 0.2%, at about 0.3%, at about 0.4%, at about 0.5%, at about 0.6%, at about 0.7%, at about 0.8%, at about 0.9%, at about 1%, at about 1.5%, at about 2%, at about 2.5%, at about 3%, at about 3.5%, at about 4%, at about 4.5%, or at about 5%.

In some aspects, the cryoprotectant comprises propyl gallate. In some aspects, the cryoprotectant comprises a sugar and/or a sugar alcohol, sodium citrate, and propyl gallate. In some aspects, propyl gallate is present in the cryoprotectant at about 0.05% to about 1.0%. In particular aspects, propyl gallate is present in the cryoprotectant at about 0.05%, at about 0.06%, at about 0.07%, at about 0.08%, at about 0.09%, at about 0.1%, at about 0.2%, at about 0.3%, at about 0.4%, at about 0.5%, at about 0.06%, at about 0.07%, at about 0.08%, at about 0.09%, or at about 1.0%.

In some aspects, the cryoprotectant comprises sodium caseinate. In some aspects, the sodium caseinate is present in the cryoprotectant at about 0.5% to about 10%. In some aspects, the sodium caseinate is present in the cryoprotectant at about 0.5%, at about 0.6%, at about 0.7%, at about 0.8%, at about 0.9%, at about 1%, at about 2%, at about 3%, at about 4%, at about 5%, at about 6%, at about 7%, at about 8%, at about 9%, or at about 10%.

In some aspects, the cryoprotectant comprises sodium glutamate. In some aspects, the sodium glutamate is present at about 1% to about 15%. In some aspects, the sodium glutamate is present at about !%, at about 2%, at about 3%, at about 4%, at about 5%, at about 6%, at about 7%, at about 8%, at about 9%, at about 10%, at about 11%, at about 12%, at about 13%, at about 14%, or at about 15%.

In some aspects, the cryoprotectant comprises cysteine. In some aspects, the cysteine is present at about 0.01% to about 2%. In some aspects, the cysteine is present at about 0.01%, at about 0.02%, at about 0.03%, at about 0.04%, at about 0.05%, at about 0.06%, at about 0.07%, at about 0.08%, at about 0.09%, at about 0.1%, at about 0.15%, at about 0.2%, at about 0.25%, at about 0.3%, at about 0.35%, at about 0.4%, at about 0.45%, at about 0.5%, at about 0.55%, at about 0.6%, at about 0.65%, at about 0.7%, at about 0.75%, at about 0.8%, at about 0.85%, at about 0.9%, at about 0.95%, at about 1.0%, at about 1.1%, at about 1.2%, at about 1.3%, at about 1.4%, at about 1.5%, at about 1.6%, at about 1.7%, at about 1.8%, at about 1.9%, or at about 2.0%.

In some aspects, the cryoprotectant comprises ascorbic acid. In some aspects, the ascorbic acid is present at about 0.005% to about 5%. In some aspects, the ascorbic acid is present at about 0.005%, at about 0.006%, at about 0.007%, at about 0.008%, at about 0.009%, at about 0.01%, at about 0.02%, at about 0.03%, at about 0.04%, at about 0.05%, at about 0.06%, at about 0.07%, at about 0.08%, at about 0.09%, at about 0.1%, at about 0.11%, at about 0.12%, at about 0.13%, at about 0.14%, at about 0.15%, at about 0.16%, at about 0.17%, at about 0.18%, at about 0.19%, at about 0.2%, at about 0.3%, at about 0.4%, at about 0.5%, at about 0.6%, at about 0.7%, at about 0.8%, at about 0.9%, at about 1%, at about 2%, at about 3%, at about 4%, or at about 5%.

In some aspects, the cryoprotectant comprises maltodextrin. In some aspects, maltodextrin is present at about 1% to about 20%. In some aspects, the maltodextrin is present at about 1%, at about 2%, at about 3%, at about 4%, at about 5%, at about 6%, at about 7%, at about 8%, at about 9%, at about 10%, at about 11%, at about 12%, at about 13%, at about 14%, at about 15%, at about 16%, at about 17%, at about 18%, at about 19%, or at about 20%.

In some aspects, the cryoprotectant comprises a combination of any one or more of sucrose, trehalose, sorbitol, propyl gallate, sodium caseinate, sodium citrate, sodium glutamate, cysteine, ascorbic acid, and/or maltodextrin.

In some aspects, the cryoprotectant comprises sucrose, propyl gallate, sodium caseinate, and sodium citrate. In some aspects, the cryoprotectant comprises sucrose, sorbitol, sodium glutamate, and sodium citrate. In some aspects, the cryoprotectant comprises trehalose, sodium glutamate, and cysteine. In some aspects, the cryoprotectant comprises trehalose, sodium glutamate, ascorbic acid, and maltodextrin.

In some aspects, the cryoprotectant comprises sucrose at about 15% to about 20%, propyl gallate at about 0.05% to about 1.0%, sodium caseinate at about 4% to about 8%, and sodium citrate at about 0.2% to about 1.0%. In some aspects, the cryoprotectant comprises sucrose at about 15% to about 20%, sorbitol at about 0.5% to about 1.5%, sodium glutamate at about 5% to about 12%, and sodium citrate at about 0.1% to about 1.5%. In some aspects, the cryoprotectant comprises trehalose at about 5% to about 20%, sodium glutamate at about 3% to about 15%, and cysteine at about 0.01% to about 1.0%. In some aspects, the cryoprotectant comprises trehalose at about 5% to about 20%, sodium glutamate at about 3% to about 15%, ascorbic acid at about 0.01% to about 2%, and maltodextrin at about 2% to about 18%.

In some aspects, the cryoprotectant further comprises corn syrup, DMSO, starches and/or modified starches of all types, and/or PVP.

The choice of pharmaceutical excipient or stabilizing excipient (cryoprotectant), carrier, or diluent is selected with regard to the intended route of administration and standard pharmaceutical or nutraceutical practice. Such compositions, in some aspects, may comprise, in addition to the excipient, carrier or diluent, additional ingredients. Such additional ingredients include, but are not limited to, any suitable binder(s), lubricant(s), suspending agent(s), coating agent(s), solubilizing agent(s), preservatives, dyes, flavoring agent(s), antioxidants, and/or suspending agents.

Examples of suitable binders include, but are not limited to, starch, gelatin, and natural sugars. Such natural sugars include, but are not limited to, glucose, anhydrous lactose, free-flow lactose, beta-lactose, corn sweeteners, and natural and/or synthetic gums, such as acacia, tragacanth or sodium alginate, carboxymethyl cellulose and polyethylene glycol. Examples of suitable lubricants include, but are not limited to, sodium oleate, sodium stearate, magnesium stearate, sodium benzoate, sodium acetate, sodium chloride and the like. Preservatives, stabilizers, dyes, and flavoring agents, in some aspects, are also provided in the composition. Examples of preservatives include, but are not limited to, sodium benzoate, sorbic acid, and esters of p-hydroxybenzoic acid. In some aspects, antioxidants and suspending agents also are present in the composition.

In some aspects, the composition includes one or more active ingredients along with a probiotic bacteria as described herein. Active ingredients can be selected from the group consisting of: antibiotics, prebiotics, probiotics, glycans (e.g., as decoys that would limit specific bacterial/viral binding to the intestinal wall), bacteriophages, microorganisms and the like. The term "prebiotic" as used herein can be a general term to refer to chemicals and/or ingredients that can affect the growth and/or activity of microorganisms in a subject or host (e.g., can allow for specific changes in the composition and/or activity in the microbiome) and can confer a health benefit on the subject. Prebiotics include, but are not limited to, complex carbohydrates, complex sugars, resistant dextrins, resistant starch, amino acids, peptides, nutritional compounds, biotin, polydextrose, fructooligosaccharide (FOS), galactooligosaccharides (GOS), inulin, lignin, psyllium, chitin, chitosan, gums (e.g. guar gum), high amylose cornstarch (HAS), cellulose, β-glucans, hemi-celluloses, lactulose, mannooligosaccharides, mannan oligosaccharides (MOS), oligofructose-enriched inulin, oligofructose, oligodextrose, tagatose, trans-galactooligosaccharide, pectin, and xylooligosaccharides (XOS). In some aspects, anti-oxidant ingredients, such as, e.g., vitamin C, are included as prebiotic substrates to act as oxygen scavengers. Prebiotic substrates, such as these, improve the colonization and survival of the bacteria in vivo. Prebiotics, in some aspects, are selectively fermented, e.g., in the colon.

In some aspects, the prebiotic is present in an amount from about 1 to about 50% by weight, with respect to the total weight of the composition. In some aspects, the prebiotic is present in an amount from about 2 to about 40% by weight. In some aspects, the prebiotic is present in an amount from about 3 to about 30% by weight. In some aspects, the prebiotic is present in an amount from about 4 to about 25% by weight. In some aspects, the prebiotic is present in an amount from about 5 to about 20% by weight. In some aspects, the prebiotic is present in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, or 50%.

In some aspects, a prebiotic is present in a greater amount than a probiotic. In some aspects, the prebiotic:probiotic ratio is about 5,000:1, about 4,500:1, about 4,000:1, about 3,500:1, about 3,000:1, about 2,500:1, about 2,000:1, about 1,500:1, about 1,000:1, about 900:1, about 800:1, about 700:1, about 600:1, about 500:1, about 400:1, about 300:1, about 200:1, about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4:1, about 3:1, about 2:1, or about 1:1.

Prebiotics, in various aspects, are found in foods (e.g., acacia gum, guar seeds, brown rice, rice bran, barley hulls, chicory root, Jerusalem artichoke, dandelion greens, garlic, leek, onion, asparagus, wheat bran, oat bran, baked beans, whole wheat flour, banana), and breast milk. In some aspects, prebiotics are administered in other forms (e.g. capsule or dietary supplement).

In some aspects, a composition of the disclosure further comprises at least one additional bacteria that degrades resistant starch. In some aspects, the bacteria that degrades resistant starch is *Bifidobacterium adolescentis, Ruminococcus bromii, Bacteriodes thetaiotamicron, Bacteriodes ovatus, Bifidobacterium breve,* or *Roseburia intestinalis.*

In some aspects, the disclosure includes a composition, wherein the bacteria survive with less than about a 1 log unit reduction in CFU, less than about a 2 log reduction in CFU, less than about a 3 log reduction in CFU, less than about a 4 log reduction in CFU, less than about a 5 log reduction in CFU, or less than about a 6 log reduction in CFU of viable bacteria over about 12 months after lyophilization in the cryoprotectant.

In some aspects, the disclosure includes products, such as feedstuffs, food products, dietary supplements, nutraceuticals, nutritional formulae, drinks and/or medicaments comprising one or more bacterial species as disclosed herein, and use thereof.

In some aspects, a composition of the disclosure comprises additionally at least one other kind of other food grade bacterium. Such suitable food grade bacteria include, but are not limited to, lactic acid bacteria, bifidobacteria, propionibacteria, and/or mixtures thereof.

In one aspect, a food product of the disclosure comprises one or more of the bacterial species disclosed herein. The term "food product" is intended to cover all consumable products that can be solid, jellied or liquid. Suitable food products include, but are not limited to, functional food products, food compositions, health foods, pet foods, livestock feed, feedstuffs and the like. In some aspects, the food product is a health food.

As used herein, the term "functional food product" means food that is capable of providing not only a nutritional effect, but is also capable of delivering a further beneficial effect to the consumer. Accordingly, functional foods are ordinary foods that have components or ingredients (such as those described herein) incorporated into them that impart to the food a specific functional, e.g., medical or physiological, benefit other than a purely nutritional benefit.

Examples of specific food products include, but are not limited to, milk-based products, ready to eat desserts, powders for re-constitution with, e.g., milk or water, chocolate milk drinks, malt drinks, ready-to-eat dishes, instant dishes, and/or drinks for humans or animals, representing a complete or a partial diet. In some aspects, the food product is intended for humans, pets or livestock. In some aspects, the composition is intended for animals including, but not limited to, dogs, cats, pigs, cattle, horses, goats, sheep, and/or poultry. In a particular aspect, the food product is intended for humans. In some aspects, the food product is intended for adult humans.

In some aspects, the "milk-based product" is any liquid or semi-solid milk or whey-based product having a varying fat content. The milk-based product, in some aspects, is, e.g., cow's milk, goat's milk, sheep's milk, skimmed milk, whole milk, milk recombined from powdered milk and whey without any processing, or a processed product, such as yogurt, curdled milk, curd, sour milk, sour whole milk, butter milk and/or other sour milk products. The milk-based product includes milk beverages, such as whey beverages, fermented milks, condensed milks, infant and/or baby milks; flavored milks, ice cream; and milk-containing food, such as sweets.

In some aspects, the product is a feedstuff or animal feed comprising the bacterial species described herein.

In some aspects, the compositions described herein are food supplements, or may be added to food supplements, i.e., also referred to herein as dietary or nutritional supplements or food additives. Thus, the disclosure includes a dietary supplement or food additive comprising one or more bacterial species described herein.

The bacterial species or strains and compositions described herein are used in human and/or animal nutrition. In some aspects, the bacterial species and compositions are used in the early-weaned period and growing, fattening period. A probiotic comprising one or more bacteria as described herein are expected to enhance immune function, treat and/or prevent infectious diseases, beneficially alter the microbiota flora of the subject being treated, and improve growth and performance. In some aspects, the bacterial species and compositions comprising them provide such benefits through increased feed conversion efficiency.

In some aspects, the composition is formulated as a dietary supplement. Such a composition can be incorporated with vitamin supplements. Such a composition can be formulated in a chewable form, such as a probiotic gummy or soft chew. Such a composition can be incorporated into a form of food and/or drink. Non-limiting examples of food and drinks where the composition is incorporated include, for example, bars, shakes, juices, infant formula, beverages, frozen food products, fermented food products, and cultured dairy products such as yogurt, yogurt drink, cheese, acidophilus drinks, and kefir.

A formulation of the disclosure can be administered as part of a fecal transplant process. A formulation can be administered to a subject by a tube, for example, nasogastric tube, nasojejunal tube, nasoduodenal tube, oral gastric tube, oral jejunal tube, or oral duodenal tube. A formulation can be administered to a subject by colonoscopy, endoscopy, sigmoidoscopy, and/or enema.

In some aspects, a composition is formulated such that the one or more of the bacteria present in the composition can replicate once they are delivered to the target habitat (e.g., the gut). In one non-limiting example, the microbial composition is formulated in a pill, powder, capsule, tablet, enteric-coated dosage form or package, such that the composition has a shelf life of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months. In some aspects, other components are added to the composition to aid in the shelf life of the composition. In some aspects, one or more bacteria may be formulated in a manner allowing survival in a non-natural environment. For example, a bacteria that is native to the gut may not survive in an oxygen-rich environment. To overcome this limitation, the bacteria may be formulated in a pill or package that can reduce or eliminate the exposure to oxygen. Other strategies to enhance the shelf-life of bacteria may include other microbes (e.g., if the bacterial consortia comprise a composition whereby one or more strains are helpful for the survival of one or more strains).

In some aspects, a composition of the disclosure is lyophilized (e.g., freeze-dried) and formulated as a powder, tablet, capsule, enteric-coated dosage form (e.g., for delivery to ileum/colon), or pill that can be administered to a subject by any suitable route. The lyophilized formulation can be mixed with a saline or other solution or solvent prior to administration.

In some aspects, the composition is formulated for oral administration, for example, as powder, tablet, capsule, enteric-coated dosage form or pill, for delivery of the contents of the formulation to the ileum and/or colon regions of a subject.

In some aspects, the composition is formulated for oral administration. In some aspects, the composition is formulated as a powder, tablet, capsule, enteric-coated dosage form or pill for oral administration. In some aspects, the composition is formulated for delivery of the bacteria to the ileum region of a subject. In some aspects, the composition is formulated for delivery of the bacteria to the colon region (e.g., upper colon) of a subject. In some aspects, the composition is formulated for delivery of the bacteria to the ileum and colon regions of a subject.

An enteric-coating can protect the contents of the oral formulation, for example, tablet or capsule, from the acidity of the stomach and provide delivery to the ileum and/or upper colon regions. Non-limiting examples of enteric coatings include pH sensitive polymers (e.g., Eudragit L 30 D-55, Eudragit S 100 or Eudragit FS30D), methyl acrylate-methacrylic acid copolymers, cellulose acetate succinate, hydroxy propyl methyl cellulose phthalate, hydroxy propyl methyl cellulose acetate succinate (e.g., hypromellose acetate succinate), polyvinyl acetate phthalate (PVAP), methyl methacrylate-methacrylic acid copolymers, shellac, cellulose acetate trimellitate, sodium alginate, zein, other polymers, fatty acids, waxes, shellac, plastics, and plant fibers. In some apects, the enteric coating is formed by a pH sensitive polymer. In some aspects, the enteric coating is formed by Eudragit L 30 D-55, Eudragit S 100 or Eudragit FS30D.

In some aspects, the enteric coating can be applied directly to the probiotic or prebiotic to protect the probiotic or prebiotic from the acidity of the stomach and provide delivery to the ileum and/or upper colon regions. For example, the probiotic or prebiotic can be encapsulated with an enteric coating that can include pH sensitive polymers (e.g., Eudragit L 30 D-55, Eudragit S 100 or Eudragit FS30D), methyl acrylate-methacrylic acid copolymers, cellulose acetate succinate, hydroxy propyl methyl cellulose phthalate, hydroxy propyl methyl cellulose acetate succinate (e.g., hypromellose acetate succinate), polyvinyl acetate phthalate (PVAP), methyl methacrylate-methacrylic acid copolymers, shellac, cellulose acetate trimellitate, sodium alginate, zein, other polymers, fatty acids, waxes, shellac, plastics, and plant fibers. In some aspects, the enteric encapsulation coating is formed by a pH sensitive polymer. In some aspects, the enteric encapsulation coating is formed by Eudragit L 30 D-55, Eudragit S 100 or Eudragit FS30D.

In some aspects, the enteric coating can be designed to dissolve at any suitable pH. In some aspects, the enteric coating is designed to dissolve at a pH greater than about pH 5.0, or at a pH greater than about pH 6.0, or at a pH greater than about pH 7.0. In some aspects, the enteric coating is designed to dissolve at a pH greater than about pH 5.0 to about pH 7.0. In some aspects, the enteric coating is designed to dissolve at a pH greater than about pH 5.0, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, or 7.5.

In some aspects, the administration of a composition or formulation of the disclosure is preceded by, for example, colon cleansing methods such as colon irrigation/hydrotherapy, enema, administration of laxatives, dietary supplements, dietary fiber, enzymes, and magnesium. In some aspects, the administration of a composition or formulation of the disclosure is preceded by, for example, a step of administering an antibiotic or antibiotics to reduce the existing microbiome prior to administration of the composition or formulation.

In some aspects, the bacteria are formulated as a population of spores. Spore-containing formulations can be administered by any suitable route described herein. Orally administered spore-containing formulations can survive the low pH environment of the stomach. The amount of spores employed can be, for example, from about 1% w/w to about 99% w/w of the entire formulation.

Formulations provided herein can include the addition of one or more agents to the composition in order to enhance stability and/or survival of the microbial formulation. Non-limiting example of stabilizing agents include genetic elements, glycerin, ascorbic acid, skim milk, lactose, tween, alginate, xanthan gum, carrageenan gum, mannitol, palm oil, and poly-L-lysine (POPL).

The terms "subject," "individual," "host," and "patient" are used interchangeably herein and refer to any animal subject, including humans, laboratory animals, livestock, and household pets. The subject can host a variety of microorganisms. The subject can have different microbiomes in various habitats on and in their body. The subject may be diagnosed or suspected of being at high risk for a particular disorder or disease. The subject may have a microbiome state that is contributing to a disease (a dysbiosis). In some aspects, the subject is not necessarily diagnosed or suspected of being at high risk for the disease. In some aspects, the subject may be suffering from a particular disorder or disease.

In some aspects, the disclosure provides methods for treating a subject. The terms "treatment" or "treating" are used interchangeably herein. These terms can refer to an approach for obtaining beneficial or desired results including, but not limited to, a therapeutic benefit and/or a prophylactic benefit. A therapeutic benefit, in various aspects, includes eradication or amelioration of the underlying disorder, disease, or condition being treated. Also, in some aspects, a therapeutic benefit is achieved with the eradication or amelioration of one or more of the physiological symptoms associated with the underlying disorder, disease, or condition, such that an improvement is observed in the subject, notwithstanding that the subject may still be afflicted with the underlying disorder, disease, or condition. A prophylactic effect includes delaying, preventing, or eliminating the appearance of a disorder, disease, or condition, delaying or eliminating the onset of symptoms of said disorder, disease, or condition, slowing, halting, or reversing the progression of the disorder, disease, or condition, or any combination thereof. For prophylactic benefit, a subject at risk of developing a particular disorder, disease, or condition, or to a subject reporting one or more of the physiological symptoms of a disorder, disease, or condition may undergo treatment, even though a diagnosis of the disorder, disease, or condition may not have been made.

In some aspects, the disclosure includes supplementing a subject of the disclosure. In some aspects, the compositions of the disclosure includes supplementing a person's diet with bacteria of the disclosure and compositions comprising one or more type of bacteria of the disclosure.

Altering the composition of a microbiome in a subject can have desired health consequences. In some aspects, compositions of the disclosure are administered as a therapeutic and/or a prophylactic for treating and/or preventing a disorder, disease, or condition. Treatments designed to alter the host microbiome(s) can result in a reduction of symptoms, prevention of disease, and or treatment of the disorder, disease, or condition. For example, modification of the gut microbiome can reduce the risk for health conditions, such as metabolic disorders.

The disclosure also provides methods for the restoration of a microbial habitat of a subject to a healthy state. In some aspects, the methods comprise microbiome correction and/or adjustment in a subject including, for example, replenishing native microbes, administering probiotics (including probiotic bacteria), removing pathogenic microbes, administering prebiotics, and/or administering growth factors necessary for microbiome survival. In some aspects, the methods also comprise administering antimicrobial agents, such as antibiotics, to reduce or remove harmful bacteria.

In some aspects, bacteria of the disclosure and compositions comprising one or more type of bacteria of the disclosure are used to alter the composition of a microbiome in a subject having desired health consequences. In some aspects, compositions of the disclosure are administered as a therapeutic, a prophylactic, or a nutraceutical. Treatments designed to alter the host microbiome(s) can result in a reduction of patient symptoms, prevention of disease, and or treatment of the disease, disorder, or condition. In various aspects, the terms "disease," "disorder," or "condition" are used interchangeably. Thus, in some aspects, such a "disorder" is an intestinal disorder, a metabolic disorder, an inflammatory disorder, or an immune disorder. For example, modification of the gut microbiome can reduce the risk of adverse health conditions, such as the disorder is an intestinal disorder, a metabolic disorder, an inflammatory disorder, or an immune disorder. In addition, modification of the gut microbiome can provide benefits for healthy weight, blood glucose management, and/or gastrointestinal health.

In various aspects, such a "disorder" includes, but is not limited to, insulin resistance, insulin sensitivity, pre-diabetes, diabetes or Type 2 Diabetes Mellitus (T2DM), irritable bowel syndrome, metabolism irregularity, obesity, obesity-related conditions, hypertension, stress, stress-related conditions, drug metabolism, gastrointestinal infection, Inflammatory Bowel Disease (IBD), Crohn's Disease. In some aspects, such condition is a low body weight, and the composition is used to increase body weight in such subjects. In some aspects, such condition is a high body weight, and the composition is used to decrease body weight in such subjects. In another aspect, the composition is used to maintain current body weight in a subject.

In some aspects, bacteria of the disclosure and compositions comprising one or more bacteria of the disclosure are used to help support healthy weight maintenance, help support healthy weight management, help a subject feel less hungry between meals, help maintain healthy blood sugar levels, help maintain blood sugar levels in the normal range, help support digestive/gut health and provide more good bacteria.

Butyrate is an anti-inflammatory factor that can affect gut permeability. Low levels of butyrate producing bacteria as well as reduced lactate producing bacteria correlate with diabetes, T2DM, obesity, and metabolic disorder. Thus, increasing the content of butyrate-producing bacteria in a subject is beneficial in the prevention and/or treatment of such diseases, conditions, or disorders.

The disclosure also provides methods for the restoration of a microbial habitat of a subject to a healthy state. In some aspects, such method comprises microbiome correction and/or adjustment including for example, replenishing native microbes, removing pathogenic microbes, administering prebiotics, and growth factors necessary for microbiome survival. Thus, in some aspects, the method also comprises administering antimicrobial agents, such as antibiotics.

Compositions containing bacteria described herein are administered for prophylactic and/or therapeutic treatments. In various aspects, the administration is by ingesting. In therapeutic applications, the compositions are administered to a subject already suffering from a disease, disorder, or condition, in an amount effective to cure or at least partially arrest the symptoms of the disease, disorder, or condition, or to cure, heal, improve, or ameliorate the condition. In some aspects, such compositions are administered to lessen a likelihood of developing, contracting, or worsening a condition. Amounts effective for this use can vary based on the severity and course of the disease, disorder, or condition, previous therapy, the subject's health status, weight, and response to the drugs, and the judgment of the treating physician.

In some aspects, a composition is administered (e.g., ingested) along with another therapeutic agent or active ingredient, and the composition and agent or active ingredient can be administered in any order or simultaneously. A composition, as described herein, can be administered before, during, or after the occurrence or observance of the disease, disorder, or condition, and the timing of administering the composition can vary. For example, in some aspects, the composition is used as a prophylactic and can be administered continuously to subjects with a propensity to a disease, disorder, or condition in order to lessen a likelihood of the occurrence of the disease, disorder, or condition. In some aspects, the composition is administered to a subject during or as soon as possible after the onset of the symptoms.

In some aspects, a composition is packaged as a kit. In some aspects, a kit includes written material or instructions on the administration/use of the composition. The written material, in some aspects, is a label. The written material, in some aspects, provides methods of administration, including methods of consumption.

In some aspects, a composition is administered orally, enterally or rectally. For example, the composition, in some aspects, is an edible composition. "Edible" means a material that is approved for human and/or animal consumption. In some aspects, the edible composition is present in food products or feed products as described herein.

Other suitable oral administration includes, but is not limited to, the use of compressed tablets, tablets, pills, gelules, drops, capsules, powder, liquids, solutions, and emulsions. In some aspects, encapsulated products are favored when the bacteria is an anaerobe. In some aspects, the composition is administered as part of a food or nutritional product, such as milk or a whey-based fermented dairy product, or as a pharmaceutical product.

In some aspects, suitable pharmaceutical compositions are in the form of suppositories, pessaries, suspensions, emulsions, lotions, ointments, creams, gels, sprays, solutions and/or dusting powders. In some aspects, a suitable composition is topically applied. For example, the active ingredient (e.g., one or more bacterial species of the disclosure), in some aspects, is incorporated into a cream consisting of, e.g., an aqueous emulsion of polyethylene glycols or liquid paraffin, or into an ointment consisting of a white wax or white soft paraffin base together with such stabilizers and/or preservatives as may be required.

In some aspects, a composition is formulated into unit dosage form, i.e., in the form of discrete portions containing a unit dose, or a multiple dose, or a sub-unit of a unit dose.

For example, a typical or usual suitable or effective dose in humans of the one or more bacterial species is from about $1 \times E3$ ($1 \times E3 = 1 \times 10^3 = 1 \times (10$ to the power $3$)) to about $1 \times E13$ colony forming units (CFU). In some instances, a suitable or effective dose is from about $1 \times E6$ to about $1 \times E11$ CFU. In particular instances, a suitable or effective dose is from about $1 \times E7$ to about $1 \times E10$ CFU. In some additional aspects, a suitable or effective dose of the bacterial species is about $1 \times E2$ CFU, $1 \times E3$ CFU, $1 \times E4$ CFU, $1 \times E5$ CFU, $1 \times E6$ CFU, $1 \times E7$ CFU, $1 \times E8$ CFU, $1 \times E9$ CFU, $1 \times E10$ CFU, $1 \times E11$ CFU, $1 \times E12$ CFU, $1 \times E13$ CFU, $1 \times E14$ CFU, or $1 \times E15$ CFU.

In some aspects, a composition of the disclosure is administered or consumed 1, 2, 3, 4, 5, or more times daily. In some aspects, the dose is daily, every other day, three times a week, twice a week, once a week, once every other week, or at other appropriate intervals for treatment of the condition.

Thus, in some aspects, a composition comprises one or more bacterial species and/or cellular components thereof, as active ingredients, in an amount of from about $1 \times E3$ to about $1 \times E13$ colony forming units (CFU)/gram (g), with respect to the weight of the composition. In some aspects, one or more bacterial species, and/or cellular components thereof, are present in an amount from about $1 \times E5$ to about $1 \times E11$ CFU/g. In some aspects, one or more bacterial species, and/or cellular components thereof, are present in an amount from about $1 \times E6$ to about $1 \times E10$ CFU/g. In some aspects, one or more bacterial species, and/or cellular components thereof, are present in the composition in an amount from about $1 \times E8$ to about $1 \times E10$ CFU/g. In some aspects, a composition comprises one or more bacterial species, and/or cellular components thereof, present in an amount of about $1 \times E1$ CFU/g, about $1 \times 2$ CFU/g, about $1 \times E3$ CFU/g, about $1 \times E4$ CFU/g, about $1 \times E5$ CFU/g, about $1 \times E6$ CFU/g, about $1 \times E7$ CFU/g, about $1 \times E8$ CFU/g, about $1 \times E9$ CFU/g, about $1 \times E10$ CFU/g, about $1 \times E11$ CFU/g, about $1 \times E12$ CFU/g, about $1 \times E13$ CFU/g, about $1 \times E14$ CFU/g, or about $1 \times E15$ CFU/g.

Thus, in some aspects, the dose of bacteria in the composition is about 0.1 milligrams (mg), about 0.2 mg, about 0.3 mg, about 0.4 mg, about 0.5 mg, about 0.6 mg, about 0.7 mg, about 0.8 mg, about 0.9 mg, about 1.0 mg, about 2.0 mg, about 3.0 mg, about 4.0 mg, about 5.0 mg, about 6.0 mg, about 7.0 mg, about 8.0 mg, about 9.0 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 300 mg, about 400 mg, about 500 mg, about 600 mg, about 700 mg, about 800 mg, about 900 mg, or about 1 gram. In some aspects, a dose of bacteria, i.e., probiotic, in the composition ranges from about 1 mg to about 500 mg. In some aspects, a dose of probiotic ranges from about 2 mg to about 300 mg. In some aspects, a dose of probiotic ranges from about 5 to about 100 mg.

In the disclosure, the terms "comprises," "comprising," "includes," "including," "having," and their conjugates mean "including, but not limited to." The term "consisting of" means "including and limited to." The term "consisting essentially of" means that the composition, method or structure may include additional ingredients, steps and/or parts, but only if the additional ingredients, steps and/or parts do not materially alter the basic and novel characteristics of the claimed bacteria, composition, method, or use.

The disclosure is further described by way of the following non-limiting examples. It is understood that the examples, embodiments, and aspects described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the extent that it is not inconsistent with the disclosure.

EXAMPLES

Additional aspects and details of the invention will be apparent from the following examples, which are intended to be illustrative rather than limiting.

Example 1: Isolation of Short Chain Fatty Acid Producing Bacteria

Experiments were carried out to isolate SCFA-producing bacteria. Fecal material was placed under anaerobic conditions shortly after a donation and processed immediately. Fecal samples from multiple donors were mixed, resuspended 1:10 in M9 minimal media ($Na_2HPO_4$ 6 g/L, $KH_2PO_4$ 3 g/L, NaCl 0.5 g/L, $NH_4Cl$ g/L, $CaCl_2$ 0.1 mM, $MgSO_4$ 1 mM) and passed through a 100 µm cell sieve to remove larger insoluble material. The samples were washed twice and resuspended in M9 minimal media to the original concentration. The slurries were then serially diluted and 100 µl of each sample were plated onto various microbial culture plates. The culture plates used were Reinforced Clostrial Agar (RCA) (Hardy Diagnostics C8721), Yeast Casitone Fatty Acid agar (YCFA) (Casitone 10 g/L, Yeast Extract 2.5 g/L, $NaHCO_3$ 4 g/L, Cysteine 1 g/L, $K_2HPO_4$ 0.45 g/L, $KH_2PO_4$ 0.45 g/L, NaCl 0.9 g/L, $(NH_4)_2SO_4$ 0.9 g/L, $MgSO_4 \cdot 7H_2O$ 0.09 g/L, $CaCl_2$ 0.09 g/L, Hemin 10 mg/L, Resazurin 1 mg/L, Biotin 10 µg/L, Cabalamin 10 µg/L, p-aminobenzoic acid 30 µL, Folic acid 50 µg/L, Pyridoxine 150 µg/L, Thiamine 50 µg/L, Riboflavin 50 µg/L, Acetic acid 1.9 ml/L, Propionic acid 0.7 ml/L, iso-Butyric acid 90 µL, n-Valeric acid 100 µl/L, iso-Valeric acid 100 µl/L), supplemented with 1% unmodified potato starch (Bob's Red Mill Natural Foods), Enriched Trypticase Soy agar (ETSA) (Anaerobe Systems AS-548), Brain Heart Infusion (BHI) (Anaerobe Systems AS-6426), MTGE (Anaerobe Systems AS-777), M17 (Difco BD 218561), supplemented with 1% unmodified potato starch. The plates were incubated for 48 hours at 37° C., under anaerobic conditions (5% $H_2$, 15% $CO_2$, 80% $N_2$).

Morphologically diverse colonies were picked from each plate and put into RCB media (AS-606, Anaerobe Systems) and modified YCFA (i.e., Yeast, Casitone, Fatty Acids) broth (Casitone 10 g/L, Yeast Extract 2.5 g/L, $NaHCO_3$ 4 g/L, Cysteine 1 g/L, $K_2HPO_4$ 0.45 g/L, $KH_2PO_4$ 0.45 g/L, NaCl 0.9 g/L, $(NH_4)_2SO_4$ 0.9 g/L, $MgSO_4 \cdot 7H_2O$ 0.09 g/L, $CaCl_2$ 0.09 g/L, Hemin 10 mg/L, Resazurin 1 mg/L, Biotin 10 µg/L, Cabalamin 10 µg/L, p-aminobenzoic acid 30 g/L, Folic acid 50 µg/L, Pyridoxine 150 µg/L. Thiamine 50 µg/L, Riboflavin 50 µg/L, 1% potato starch) in 96-deep well plates. After overnight incubation at 37° C. under anaerobic conditions, butyrate, acetate and propionate levels were measured in the supernatants from each well (see analytical method below).

Organisms from the wells positive for butyrate were isolated and identified by MALDI TOF or 16s-rRNA sequence (Accugenix, Charles River Labs, Inc.). Single bacterial colonies were lysed with 1 µl of 70% formic acid, dried, and 1 µl of matrix on a MALDI TOF plate, dried and loaded onto the instrument where they were ionized by a laser. The matrix absorbs most of the energy and transfers it to the sample. The ionized sample was broken into smaller pieces which were then pulled into a mass analyzer region and were separated based on their mass to charge ratio (m/z). Bacteria were identified by comparing their spectra to the spectra from known bacteria in the instrument's database.

Example 2: Lyophilization of Short Chain Fatty Acid Producing Bacteria

Experiments were carried out to determine how well bacteria could survive lyophilization. Bacteria were cultured by inoculating 100 ml of the appropriate bacteriological media with a single bacterial isolate followed by incubation at 37° C. under anaerobic conditions. Samples (200 µl) were collected from the culture at various time points for analysis of OD600, spotting of 10 µl onto solid bacteriological media for colony-forming unit (CFU) determination, and for aliquoting into four different lyophilization media. The lyophilization vials were flash frozen in dry ice methanol and stored at −80° C. until lyophilization. The four lyophilization media used were: media 1 (sucrose 17.8%, propyl gallate 0.2%, sodium caseinate 6.4%, sodium citrate 0.6%); media 2 (sucrose 17.5%, Sorbitol 0.9%, sodium glutamate 8.5%, sodium citrate 0.6%); media 3 (trehalose 15%, sodium glutamate 8.5%, cysteine 0.1%); and media 4 (trehalose 10%, sodium glutamate 8.5%, ascorbic acid 0.2%, maltodextrin 10%). The samples were lyophilized in a VirTis Wizard 2.0 Advantage plus lyophilizer under the conditions set out in Table 3 below.

TABLE 3

Lyophilization Conditions

| Temperature (° Celsius) | Time (min) | Vacuum (mTorr) |
|---|---|---|
| −10 | 30 | 100 |
| 0 | 120 | 100 |
| 0 | 30 | 100 |
| 10 | 600 | 100 |
| 10 | 720 | 100 |

The number of CFUs was determined before and after lyophilization to determine the number of bacteria that survived the lyophilization procedure. Samples were serially diluted and 10 µl was spotted in triplicate onto square RCB agar plates with a grid. After 24-48 hours of incubation, bacterial colonies were counted visually.

Example 3: Short Chain Fatty Acid Quantitation from Bacterial Isolates

Experiments were carried out to quantitate short chain fatty acid production in bacterial isolates. Supernatants from the bacterial isolates were diluted 20-fold with acetonitrile, and 20 µl of each of the diluted samples were mixed with 500 µl of derivatization mix (Triphenylphosphine; 2,2'-Dipyridyl Disulfide; Hydrazinoquinoline combined in equal volumes for a final concentration of 2 mM, containing the working internal standards) in a 2 ml, 96-well deep well plate and capped and heated at 65° C. for 1 hour. After incubation, the plates were removed and placed at 4° C. for 15 minutes, then vortexed gently, and centrifuged for 1 minute at 2000 rpm. Samples (150 µl from each well) were transferred to a clean 96-well plate containing 300 µl of acetonitrile per well. The derivatized samples were analyzed by High Performance Liquid Chromatography/MS/MS (AB Sciex triple Quad 4000) with a Waters Xselect HSS C18 SB 2.1×50 mm×2.5 column using 0.1% formic acid in water as mobile phase A and 0.1% formic acid in acetonitrile as mobile phase B. The internal standards were butyric acid-d7, propionic acid-d6, and acetic acid-d3. The High Performance Liquid Chromatography parameters used are set out in Table 4 below.

TABLE 4

| HPLC Parameters | | | |
|---|---|---|---|
| Flow Rate | 0.4 mL/min | | |
| Mobile Phase | Time | Mobile A | Mobile B |
| | 0 | 98% | 2% |
| | 0.01 | 98% | 2% |
| | 5 | 70% | 30% |
| | 5.01 | 5% | 95% |
| | 5.5 | 5% | 95% |
| | 5.51 | 98% | 2% |
| | 7.50 | Stop | |
| Injection volume | 1 uL | | |

The concentrations of butyric acid, propionic acid and acetic acid were determined. For example, the amounts of butyrate produced by the bacteria are provided in Table 5 below.

TABLE 5

Butyrate Production

| SEQ ID NO: | Amount of Butyrate Produced (micromoles over about 24 hours) |
|---|---|
| 1 | 19975 |
| 2 | 26217 |
| 3 | 22131 |
| 4 | 19862 |
| 5 | 19521 |
| 6 | 20543 |
| 7 | 30713 |
| 8 | 13052 |
| 9 | 22321 |
| 10 | 20996 |
| 11 | 16173 |
| 12 | 12106 |
| 13 | 22699 |
| 14 | 25026 |
| 15 | 22926 |
| 16 | 28885 |
| 17 | 26671 |
| 18 | 18613 |
| 19 | 4796 |
| 20 | 28828 |
| 21 | 32724 |
| 22 | 20656 |
| 23 | 19975 |

Example 4: Determination of Preferred Media for Bacterial Growth

Experiments were carried out to determine preferred media for bacterial growth. Single bacterial isolates were grown for 48 hours at 37° C. in an anaerobic chamber in various media, e.g., RCB (Hardy Diagnostics C8721), RCB (Anaerobe Systems (AS-606), BHI, (Anaerobe Systems AS-6426), Peptone Yeast Glucose agar (PYG) (Anaerobe Systems, AS-606), YCFA+1.0% Resistant Starch (as discussed herein above in Example 1), TSB (Difco BD 211825), MTGE (Anaerobe Systems AS-777) or GM17 (M17 media (Difco BD 218561) supplemented with 0.5% glucose). Growth was measured in a spectrophotometer ($OD_{600}$ nM) at various time points.

Example 5: Selection and Sequencing of Short Chain Fatty Acid Producing Bacteria Bacteria that were found to produce the greatest levels of SCFA and be resistant to lyophilization were isolated and the 16S-rRNA encoding gene from each of these bacteria (see Table 1) was sequenced (Charles River's Accugenix®).

Example 6: Determining Oxygen Sensitivity of Short Chain Fatty Acid Producing Bacteria Because strict anaerobic bacteria are difficult to grow in bulk outside of anaerobic conditions, the oxygen sensitivity of various bacteria were tested under various microoxic conditions. Bacteria that were found to produce the greatest levels of SCFA and be resistant to lyophilization were subject to microoxic conditions. Single bacterial isolates were grown for 24-48 h at 37° C. in a microoxic anaerobic chamber, wherein the oxygen was controlled between 50-150 ppm, and serially diluted in phosphate buffered saline. 10 µL was spotted onto an RCB agar plate for colony formation unit (CFU) determination. Immediately after spotting of plates, one plate was retained in the anaerobic chamber and the other plates were removed from the anaerobic chamber and exposed to oxygen in the ambient air. Plates exposed to oxygen in the ambient air were placed back into the anaerobic chamber after various times of oxygen exposure and incubated for 24-48 h to allow CFU development. Bacteria growth from all plates was determined by CFU formation.

Example 7: Determining Whole Genome Sequence of Short Chain Fatty Acid Producing Bacteria Bacteria that were found to produce the greatest levels of SCFA and be tolerant of lyophilization (e.g., one of the two isolates for each genus and species) were sequenced to determine their whole genome (MOgene, St. Louis, MO). The whole genome sequences of various SCFA-producing bacteria (SEQ ID NOs: 24-35) of the disclosure are provided in Table 6 below with their counterpart 16S-rRNA encoding gene sequence.

TABLE 6

Whole genomic sequences of probiotic bacteria of the disclosure

| Whole Genome SEQ ID NO: | 16S-rRNA encoding gene SEQ ID NO: | Bacteria |
|---|---|---|
| 24 | 1 | Roseburia faecis |
| 25 | 2 | Roseburia intestinalis |
| 26 | 9 | Anaerostipes hadrus |
| 27* | 4 | Clostridium innocuum |
| 28* | 6 | Clostridium butyricum |
| 29 | 10 | Coprococcus comes |
| 30 | 11 | Agathobacter rectalis |
| 31* | 13 | Butyricicoccus faecihominis |
| 32* | 15 | Anaerostipes caccae |
| 33* | 19 | Flavonifractor plautii |
| 34 | 21 | Roseburia hominis |
| 35 | 22 | Roseburia inulinivorans |

*These sequences, i.e., SEQ ID NOs: 27, 28, and 31-33, comprise a noncontiguous finished whole genome for each bacterial species of the disclosure. The genome sequences for the species marked with an asterisk were noncontiguous likely because of gaps and/or lack of confidence in assembly due to repeat regions, and the gaps are identified in the sequence in the sequence listing.

Additionally, the presence or absence of potential toxin or antibiotic resistance genes is identified in the bacteria.
Combinations
  A. A composition comprising
    (a) at least one human isolate of short chain fatty acid (SCFA)-producing bacteria or mixtures thereof, wherein the bacteria comprises a 16S ribosomal RNA (16S-rRNA) encoding gene sequence that is at least about 80% identical to any one of the nucleotide sequences of SEQ ID NOs: 1-23 or a DNA sequence that is at least about 80% identical to any one of the nucleotide sequences of SEQ ID NOs: 24-35, and (b) an excipient, carrier, and/or diluent.

B. The composition of paragraph B, wherein the bacteria is selected from the group consisting of *Agathobacter rectalis, Anaerostipes caccae, Anaerostipes hadrus, Butyricicoccus faecihominis, Clostridium butyricum, Clostridium cochlearium, Clostridium innocuum, Coprococcus comes, Flavonifactor plautii, Roseburia faecis, Roseburia hominis, Roseburia intestinalis*, and *Roseburia inulinivorans*.

C. The composition of paragraph A or B, wherein the bacteria is lyophilized.

D. The composition of any one of paragraphs A-C, wherein the excipient is a cryoprotectant.

E. The composition of paragraph D, wherein the cryoprotectant comprises a sugar or a sugar alcohol.

F. The composition of paragraph E, wherein the cryoprotectant further comprises any one or more of propyl gallate, sodium caseinate, sodium citrate, sodium glutamate, cysteine, ascorbic acid, and/or maltodextrin.

G. The composition of any one of paragraphs D-F, wherein the cryoprotectant comprises
(a) sucrose at about 1% to about 25%;
(b) trehalose at about 1% to about 25%;
(c) sorbitol at about 0.1% to about 5%;
(d) propyl gallate at about 0.05% to about 1.0%;
(e) sodium caseinate at about 0.5% to about 10%;
(f) sodium citrate at about 0.1% to about 5%;
(g) sodium glutamate at about 1% to about 15%;
(h) cysteine at about 0.01% to about 2.0%;
(i) ascorbic acid at about 0.005% to about 5.0%;
(j) maltodextrin at about 1% to about 20%; or
(k) a combination of any of any one or more of (a)-(j).

H. The composition of any one of paragraphs D-G, wherein the cryoprotectant comprises
(a) sucrose at about 15% to about 20%, propyl gallate at about 0.05% to about 1.0%, sodium caseinate at about 4% to about 8%, and sodium citrate at about 0.2% to about 1.0%;
(b) sucrose at about 15% to about 20%, sorbitol at about 0.5% to about 1.5%, sodium glutamate at about 5% to about 12%, and sodium citrate at about 0.1% to about 1.5%;
(c) trehalose at about 5% to about 20%, sodium glutamate at about 3% to about 15%, cysteine at about 0.01% to about 1.0%; or
(d) trehalose at about 5% to about 20%, sodium glutamate at about 3% to about 15%, ascorbic acid at about 0.01% to about 2%, and maltodextrin at about 2% to about 18%.

I. The composition of any one of paragraphs D-H, wherein the cryoprotectant comprises
(a) sucrose at about 17.8%, propyl gallate at about 0.2%, sodium caseinate at about 6.4%, and sodium citrate at about 0.6%;
(b) sucrose at about 17.5%, sorbitol at about 0.9%, sodium glutamate at about 8.5%, and sodium citrate at about 0.6%;
(c) trehalose at about 15%, sodium glutamate at about 8.5%, and cysteine at about 0.1%; or
(d) trehalose at about 10%, sodium glutamate at about 8.5%, ascorbic acid at about 0.2%, and maltodextrin at about 10%.

J. The composition of any one of paragraphs A-I, wherein the bacteria survive with less than about a 1 log unit reduction in CFU, less than about a 2 log reduction in CFU, less than about a 3 log reduction in CFU, less than about a 4 log reduction in CFU, less than about a 5 log reduction in CFU, or less than about a 6 log reduction in CFU of viable bacteria over about 12 months after lyophilization in the cryoprotectant.

K. The composition of any one of paragraphs A-J, wherein the composition comprises from about 1×E3 to about 1×E11 colony-forming units (CFU) of the SCFA-producing bacteria and mixtures thereof.

L. The composition of any one of paragraphs A-K, wherein the bacteria and/or mixtures thereof produce at least about 1000 micromoles of the SCFA over about 24 hours.

M. The composition of any one of paragraphs A-L, wherein the SCFA is acetate, propionate, or butyrate, or a combination thereof.

N. The composition of any one of paragraphs A-M, wherein the SCFA is butyrate.

O. The composition of any one of paragraphs A-N, wherein the composition further comprises a prebiotic and/or a resistant starch.

P. The composition of any one of paragraphs A-O, wherein the composition further comprises at least one additional bacteria that degrades resistant starch.

Q. The composition of paragraph P, wherein the bacteria that degrades resistant starch is *Bifidobacterium adolescentis, Ruminococcus bromii, Bacteriodes thetaiotamicron, Bacteriodes ovatus, Bifidobacterium breve*, or *Roseburia intestinalis*.

R. The composition of any one of paragraphs A-Q, wherein the composition is a probiotic composition.

S. A method of increasing short chain fatty acid (SCFA) in the gastrointestinal tract of a subject comprising administering to the subject an effective amount of the composition of any one of paragraphs A-R.

T. The method of paragraph S, wherein the SCFA is acetate, propionate, or butyrate, or a combination thereof.

U. The method of paragraphs S or T, wherein the SCFA is butyrate.

V. The method of any one of paragraphs S-U, wherein the subject suffers from or is at risk of suffering from a disorder.

W. The method of any one of paragraphs S-V, wherein the disorder is an intestinal disorder, a metabolic disorder, an inflammatory disorder, or an immune disorder.

X. The method of paragraphs V or W, wherein the disorder is insulin resistance, insulin sensitivity, pre-diabetes, diabetes or Type 2 Diabetes Mellitus (T2DM), irritable bowel syndrome, metabolism irregularity, obesity, obesity-related conditions, hypertension, stress, stress-related conditions, drug metabolism irregularity, gastrointestinal infection, Inflammatory Bowel Disease (IBD), or Crohn's Disease.

Y. A method for reducing or maintaining glucose level and/or body weight in a subject in need thereof comprising administering to the subject an effective amount of the composition of any one of paragraphs A-R.

Z. The method of claim Y, wherein the subject suffers from diabetes or pre-diabetes.

AA. A method for treating, ameliorating, or preventing a disorder in a subject suffering therefrom or at risk of suffering therefrom comprising administering to the subject an effective amount of the composition of any one of paragraphs A-R.

BB. The method of paragraphs AA, wherein the disorder is an intestinal disorder, a metabolic disorder, an inflammatory disorder, or an immune disorder.

CC. The method of paragraphs AA or BB, wherein the disorder is insulin resistance, insulin sensitivity, pre-diabetes, diabetes or Type 2 Diabetes Mellitus (T2DM), irritable bowel syndrome, metabolism irregularity, obesity, obesity-related conditions, hypertension, stress, stress-related conditions, drug metabolism, gastrointestinal infection, Inflammatory Bowel Disease (IBD), or Crohn's Disease.

DD. Use of a composition of any one of paragraphs A-R in the preparation of a medicament or nutritional product for treating a metabolic disorder, an immune disorder, an intestinal disorder, or an inflammatory disorder.

The disclosure has been described in terms of particular embodiments found or proposed to comprise specific modes for the practice of the methods and compositions of the invention described herein. Various modifications and variations of the described invention will be apparent to those skilled in the art without departing from the scope and spirit of the invention. Although the disclosure provides specific embodiments or aspects, it should be understood that the invention as claimed should not be unduly limited to such specific embodiments or aspects. Indeed, various modifications of the described modes for carrying out the invention that are obvious to those skilled in the relevant fields are intended to be within the scope of the following claims.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising
   (a) at least one lyophilized human isolate of short chain fatty acid (SCFA)-producing bacteria or mixtures thereof, wherein the bacteria comprises a 16S ribosomal RNA (16S-rRNA) encoding gene sequence comprising the nucleotide sequences of SEQ ID NOs: 13 or 14 or a DNA sequence comprising the nucleotide sequence of SEQ ID NO: 31, and
   (b) an excipient, carrier, and/or diluent,
   wherein the composition is in a form selected from the group consisting of a food product, a beverage product, a cosmetic, a nutritional supplement, and mixtures thereof.

2. The composition of claim 1, wherein the bacteria comprises *Butyricicoccus faecihominis*.

3. The composition of claim 1, wherein the excipient is a cryoprotectant.

4. The composition of claim 3, wherein the cryoprotectant comprises a material selected from the group consisting of sugar, sugar alcohol, and a combination thereof.

5. The composition of claim 4, wherein the cryoprotectant further comprises an additional material selected from the group consisting of propyl gallate, sodium caseinate, sodium citrate, sodium glutamate, cysteine, ascorbic acid, maltodextrin, and combinations thereof.

6. The composition of claim 3, wherein the cryoprotectant comprises
   (a) sucrose at about 1% to about 25%;
   (b) trehalose at about 1% to about 25%;
   (c) sorbitol at about 0.1% to about 5%;
   (d) propyl gallate at about 0.05% to about 1.0%;
   (e) sodium caseinate at about 0.5% to about 10%;
   (f) sodium citrate at about 0.1% to about 5%;
   (g) sodium glutamate at about 1% to about 15%;
   (h) cysteine at about 0.01% to about 2.0%;
   (i) ascorbic acid at about 0.005% to about 5.0%;
   (j) maltodextrin at about 1% to about 20%; or
   (k) a combination of any of any one or more of (a)-(j).

7. The composition of claim 3, wherein the cryoprotectant comprises
   (a) sucrose at about 15% to about 20%, propyl gallate at about 0.05% to about 1.0%, sodium caseinate at about 4% to about 8%, and sodium citrate at about 0.2% to about 1.0%;
   (b) sucrose at about 15% to about 20%, sorbitol at about 0.5% to about 1.5%, sodium glutamate at about 5% to about 12%, and sodium citrate at about 0.1% to about 1.5%;
   (c) trehalose at about 5% to about 20%, sodium glutamate at about 3% to about 15%, cysteine at about 0.01% to about 1.0%; or

SEQUENCE LISTING

The patent contains a lengthy sequence listing. A copy of the sequence listing is available in electronic form from the USPTO web site (https://seqdata.uspto.gov/?pageRequest=docDetail&DocID=US12059441B2). An electronic copy of the sequence listing will also be available from the USPTO upon request and payment of the fee set forth in 37 CFR 1.19(b)(3).

(d) trehalose at about 5% to about 20%, sodium glutamate at about 3% to about 15%, ascorbic acid at about 0.01% to about 2%, and maltodextrin at about 2% to about 18%.

8. The composition of claim 3, wherein the cryoprotectant comprises
   (a) sucrose at about 17.8%, propyl gallate at about 0.2%, sodium caseinate at about 6.4%, and sodium citrate at about 0.6%;
   (b) sucrose at about 17.5%, sorbitol at about 0.9%, sodium glutamate at about 8.5%, and sodium citrate at about 0.6%;
   (c) trehalose at about 15%, sodium glutamate at about 8.5%, and cysteine at about 0.1%; or
   (d) trehalose at about 10%, sodium glutamate at about 8.5%, ascorbic acid at about 0.2%, and maltodextrin at about 10%.

9. The composition of claim 6, wherein the bacteria, when tested for survival upon lyophilization in the cryoprotectant, survive with less than about a 1 log unit reduction in CFU of viable bacteria over about 12 months after lyophilization in the cryoprotectant.

10. The composition of claim 1, wherein the composition comprises from about 1×E3 to about 1×E11 colony-forming units (CFU) of the SCFA-producing bacteria and mixtures thereof.

11. The composition of claim 1, wherein the bacteria and/or mixtures thereof produce at least about 1000 micromoles of the SCFA over about 24 hours.

12. The composition of claim 1, wherein the SCFA is acetate, propionate, or butyrate, or a combination thereof.

13. The composition of claim 1, wherein the composition further comprises a prebiotic.

14. The composition of claim 1, wherein the composition further comprises at least one additional bacteria that degrades resistant starch.

15. The composition of claim 14, wherein the bacteria that degrades resistant starch is *Bifidobacterium adolescentis, Ruminococcus bromii, Bacteroides thetaiotamicron, Bacteroides ovatus, Bifidobacterium breve*, or *Roseburia intestinalis*.

16. A method of increasing short chain fatty acid (SCFA) in the gastrointestinal tract of a subject comprising administering to the subject an effective amount of the composition of claim 1.

17. The method of claim 16, wherein the SCFA is acetate, propionate, or butyrate, or a combination thereof.

18. A method for reducing or maintaining glucose level and/or body weight in a subject in need thereof comprising administering to the subject an effective amount of the composition of claim 1.

19. The method of claim 18, wherein the subject suffers from diabetes or pre-diabetes.

20. The method of claim 13, wherein the prebiotic comprises a resistant starch.

* * * * *